(12) United States Patent
Yeo

(10) Patent No.: US 10,113,971 B2
(45) Date of Patent: Oct. 30, 2018

(54) TEST APPARATUS AND CONTROL METHOD THEREOF

(71) Applicant: SAMSUNG ELECTRONICS CO., LTD., Suwon-si (KR)

(72) Inventor: Yeong Bae Yeo, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 36 days.

(21) Appl. No.: 14/862,242

(22) Filed: Sep. 23, 2015

(65) Prior Publication Data

US 2016/0161418 A1 Jun. 9, 2016

(30) Foreign Application Priority Data

Dec. 4, 2014 (KR) .................. 10-2014-0173205

(51) Int. Cl.
| | |
|---|---|
| G01N 21/00 | (2006.01) |
| G01N 21/78 | (2006.01) |
| G01N 21/77 | (2006.01) |
| G01N 21/07 | (2006.01) |
| G01N 21/25 | (2006.01) |
| G01N 21/03 | (2006.01) |

(52) U.S. Cl.
CPC ............. *G01N 21/78* (2013.01); *G01N 21/07* (2013.01); *G01N 21/253* (2013.01); *G01N 2021/0325* (2013.01); *G01N 2021/7783* (2013.01)

(58) Field of Classification Search
CPC .................. G01N 21/6486; G01N 2021/7786
USPC .............................. 422/82.09, 82.05; 700/59
See application file for complete search history.

(56) References Cited

U.S. PATENT DOCUMENTS

| | | | | |
|---|---|---|---|---|
| 2002/0154315 A1* | 10/2002 | Myrick | ..................... | G01J 3/18 356/305 |
| 2004/0013231 A1 | 1/2004 | He et al. | | |
| 2006/0289790 A1 | 12/2006 | Raymond et al. | | |
| 2009/0027693 A1 | 1/2009 | Dailey, Jr. et al. | | |
| 2011/0043828 A1 | 2/2011 | Frutos et al. | | |

(Continued)

FOREIGN PATENT DOCUMENTS

| | | |
|---|---|---|
| JP | 57204437 A | 12/1982 |
| JP | 2010-256290 A | 11/2010 |

OTHER PUBLICATIONS

Search Report dated Jan. 14, 2016 issued by the International Searching Authority in counterpart International Patent Application No. PCT/KR2015/009819 (PCT/ISA/210).

(Continued)

*Primary Examiner* — Natalia Levkovich
(74) *Attorney, Agent, or Firm* — Sughrue Mion, PLLC

(57) ABSTRACT

A test apparatus and a control method thereof are provided. The test apparatus is configured to test a sample in a reactor. The test apparatus includes at least one light emitter configured to emit light to chambers of the reactor, a light receiver configured to receive light passed through the chambers while scanning the chambers, and a processor configured to determine a position or an area of a chamber among the chambers, based on light receiving positions of the light receiver, and respective intensities of the received light. The processor is further configured to measure an optical density of light passed through the determined position or the determined area of the chamber.

14 Claims, 24 Drawing Sheets

(56) References Cited

U.S. PATENT DOCUMENTS

2012/0182556 A1 7/2012 Van Praet
2013/0314712 A1 11/2013 Proll et al.

OTHER PUBLICATIONS

Communication dated Nov. 8, 2017, from the European Patent Office in counterpart European Application No. 15864837.8.

* cited by examiner

FIG. 11B
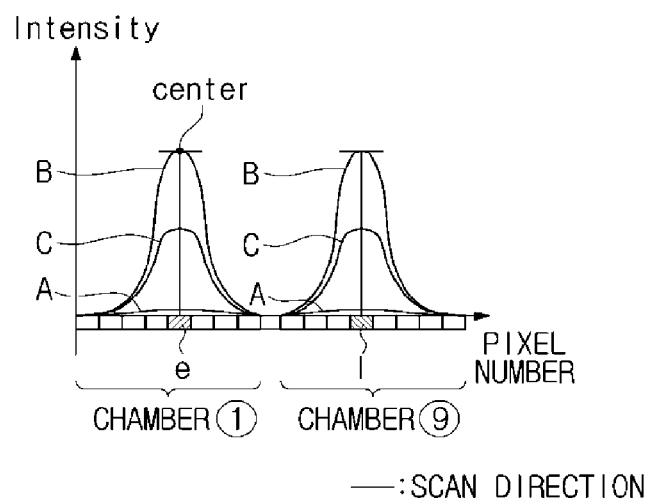
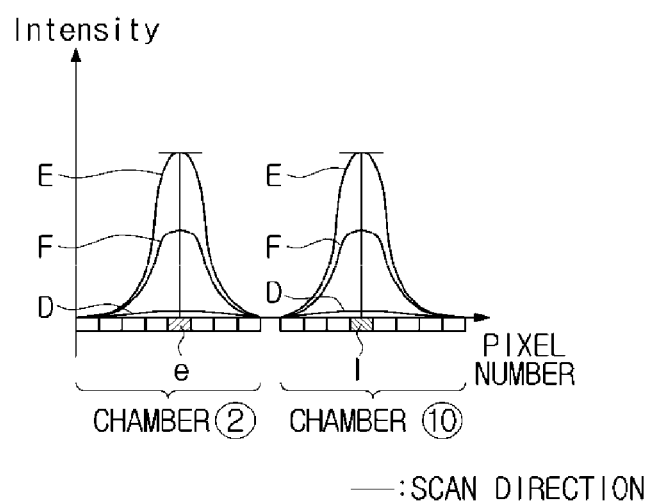
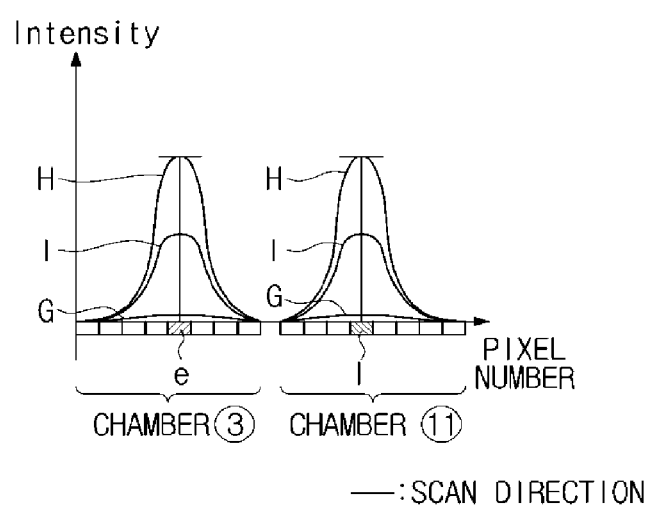

FIG. 12
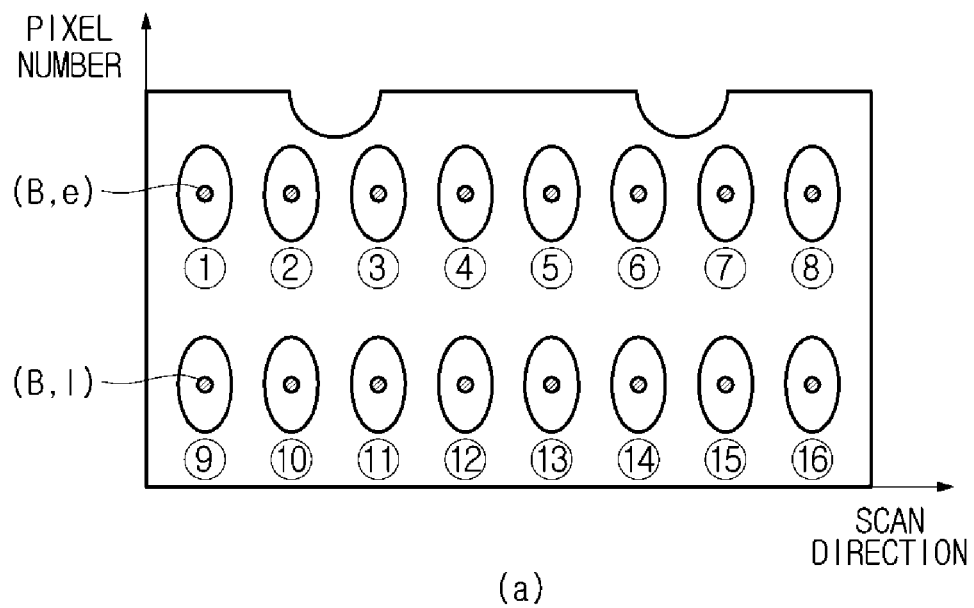
(a)
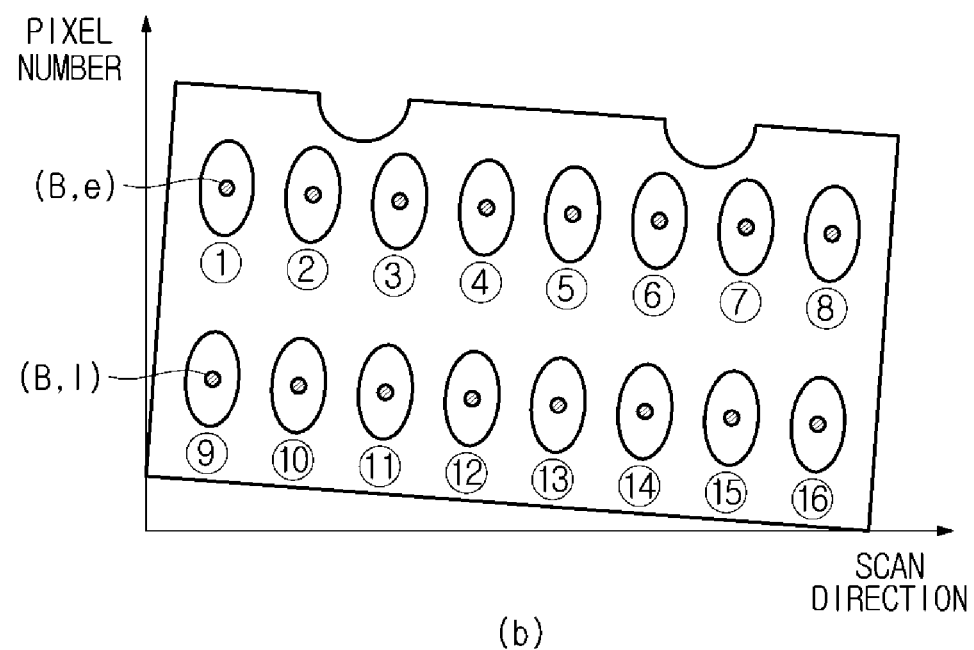
(b)

FIG. 14
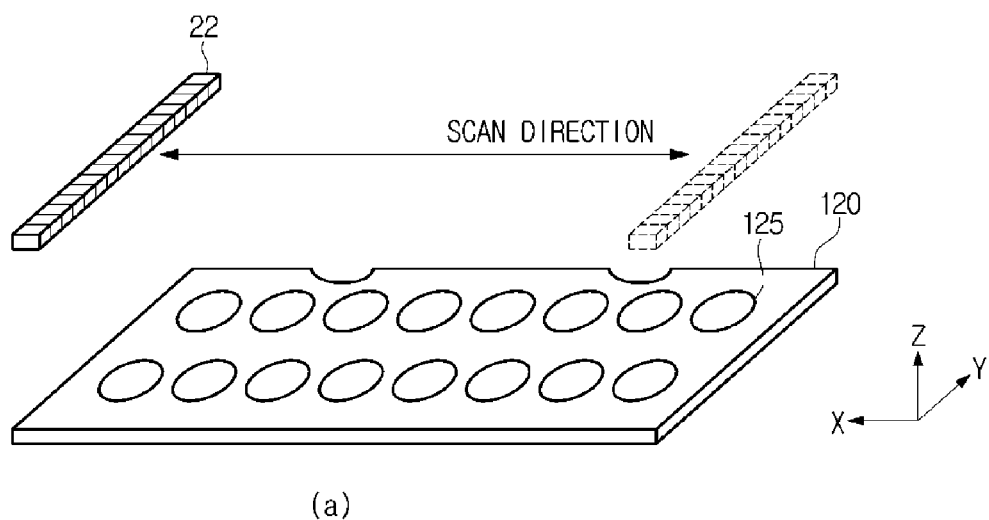
(a)
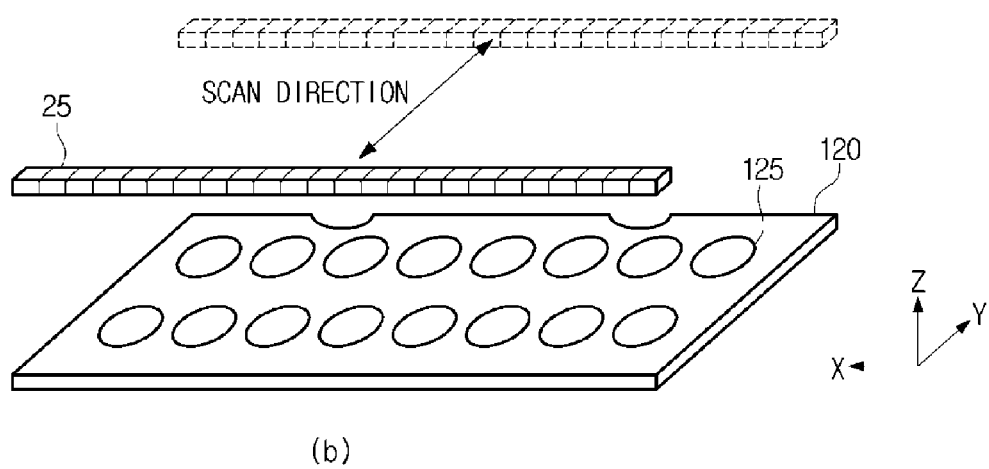
(b)

TEST APPARATUS AND CONTROL METHOD THEREOF

CROSS-REFERENCE TO RELATED APPLICATION

This application claims priority from Korean Patent Application No. 10-2014-0173205, filed on Dec. 4, 2014, in the Korean Intellectual Property Office, the disclosure of which is incorporated herein by reference in its entirety.

BACKGROUND

1. Field

Apparatuses and methods consistent with exemplary embodiments relate to a test apparatus and a control method thereof.

2. Description of the Related Art

An immunity test, a clinical chemistry test, and the like are performed on a patient's sample to perform an in vitro diagnosis. The immunity test and the clinical chemistry test may play a very important role in determining a diagnosis, a treatment, and a prognosis of a patient's state.

The in vitro diagnosis may be performed in an inspecting room or a laboratory room of a hospital. However, an in vitro diagnosis device may need to be miniaturized to rapidly analyze samples in various fields, such as environmental monitoring, food inspection, medical diagnosis, and the like, and to perform the in vitro diagnosis without a limitation in a place.

Particularly, in medical diagnosis, the reliance on a POC (point-of-care) blood analysis device that uses a disposable cartridge has increased, and thus research and development of a small POC blood analysis device capable of rapidly and accurately testing blood has been actively performed.

Therefore, there is a need to provide a test apparatus capable of accurately and precisely measuring an optical density regardless of an arrangement state of a lab-on-a-chip or lab-on-a-disk, and a control method thereof.

SUMMARY

Exemplary embodiments address at least the above disadvantages and other disadvantages not described above. Also, exemplary embodiments are not required to overcome the disadvantages described above, and may not overcome any of the problems described above.

According to an aspect of an exemplary embodiment, there is provided a test apparatus configured to test a sample in a reactor, the test apparatus including at least one light emitter configured to emit light to chambers of the reactor, a light receiver configured to receive light passed through the chambers while scanning the chambers, and a processor configured to determine a position or an area of a chamber among the chambers, based on light receiving positions of the light receiver, and respective intensities of the received light. The processor is further configured to measure an optical density of light passed through the determined position or the determined area of the chamber.

The light receiver may include an array of light receiving elements.

The array may include a one-dimensional array or a two-dimensional array.

The processor may be further configured to generate a map including coordinates of the respective chambers, based on the light receiving positions and the respective intensities, the coordinates including respective pixel numbers of the light receiving elements and the respective light receiving positions.

The processor may be configured to calculate an average value of an optical density of light passed through an area within a range from the determined position or the determined area of the chamber.

The light emitter may be configured to emit the light to the chambers at a fixed position, or while scanning the chambers in correspondence to the light receiver.

The test apparatus may further include a filter configured to detect light having wavelengths from the emitted light, and emit the detected light to the chambers.

The test apparatus may further include an auxiliary light receiver configured to receive the emitted light.

The test apparatus may further include a light path changer configured to change a path of the emitted light to allow the auxiliary light receiver to receive the emitted light.

The processor may be further configured to compensate for differences of a variation of an intensity of the light received through the chambers by comparing a variation of an intensity of the received emitted light with data of an intensity of the emitted light.

The processor may be configured to measure the optical density of the light passed through the determined position and the determined area of the chamber, based on the compensated differences.

The test apparatus may further include a condenser lens disposed between the reactor and the light receiver, the condenser lens being configured to focus the light passed through the chambers to the light receiver having an area less than that of the reactor.

According to an aspect of another exemplary embodiment, there is provided a control method of testing, by a test apparatus, a sample in a reactor, the control method including emitting light to chambers of the reactor, receiving light passed through the chambers while scanning the chambers, determining a position or an area of a chamber among the chambers, based on light receiving positions and respective intensities of the received light. The control method further includes measuring an optical density of light passed through the determined position and the determined area of the chamber.

The control method may further include generating a map including coordinates of the respective chambers, based on the light receiving positions and the respective intensities, the coordinates including respective pixel numbers of the light receiving elements and the respective light receiving positions.

The measuring the optical density of the light may include calculating an average value of an optical density of light passed through an area within a range from the determined position or the determined area of the chamber.

The emitting the light to the chambers may include emitting the light to the chambers at a fixed position, or while scanning the chambers in correspondence to the receiving the light passed through the chambers.

The control method may further include detecting light having wavelengths from the emitted light, and emitting the detected light to the chambers.

According to an aspect of another exemplary embodiment, there is provided a test apparatus configured to test a sample in a reactor, the test apparatus including at least one light emitter configured to emit light to chambers of the reactor, a light receiver including light receiving elements configured to receive light passed through the chambers while moving from a side of the reactor to another side of the reactor, and a processor configured to determine a coordinate of a chamber among the chambers, the coordinate including a respective pixel number of one of the light receiving elements and a respective light receiving position of the light receiver at which an intensity of light received through the chamber is largest.

The processor may be further configured to measure an optical density of light passed through the determined coordinate of the chamber.

The light receiver may be further configured to receive light passed through air-holes adjacent to the chambers, and the processor may be further configured to compensate for differences of a variation of an intensity of the light received through the chambers by comparing a variation of an intensity of the light received through the air-holes with data of an intensity of the emitted light.

BRIEF DESCRIPTION OF THE DRAWINGS

The above and/or other aspects will be more apparent by describing in detail exemplary embodiments with reference to the accompanying drawings, in which:

FIG. 11B a graph illustrating that a light receiver acquires information related to a light receiving position of light and an intensity of light by receiving light according to an exemplary embodiment;

FIG. 12 is a schematic diagram of a map illustrating information related to a light receiving position and an intensity of received light in a coordinate system according to an exemplary embodiment;

FIG. 14 is a view illustrating a direction in which a light receiver scans an inspector according to an exemplary embodiment;

DETAILED DESCRIPTION OF THE EXEMPLARY EMBODIMENTS

Figure 1:
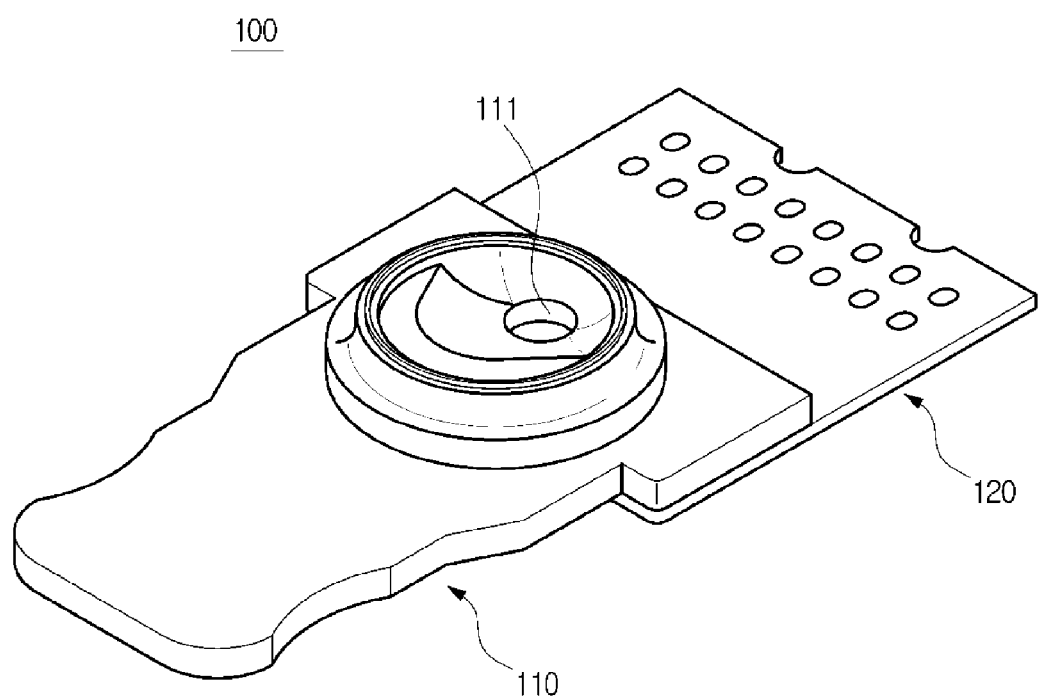
FIG. 1 is a view illustrating an exterior of a reactor according to an exemplary embodiment.

Hereinafter, exemplary embodiments are described in more detail with reference to the accompanying drawings.

In the following description, like reference numerals are used for like elements even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail because they would obscure the exemplary embodiments with unnecessary detail.

It will be understood that the terms such as "unit," "-er (-or)," and "module" described in the specification refer to an element configured to perform at least one function or operation, and may be implemented in hardware or a combination of hardware and software.

The need for a rapid and accurate field inspection has increased in various fields, such as environmental monitoring, food inspection, medical diagnosis, and the like. For example, in medical diagnosis, the reliance on a POC (point-of-care) blood analysis device that uses a disposable cartridge has increased, and thus research and development of a small POC blood analysis device capable of rapidly and accurately testing blood has been actively performed. A blood analysis device based on a lab-on-a-chip or lab-on-a-disk may need to be miniaturized and to support multi-item inspection. Therefore, the lab-on-a-chip or lab-on-a-disk may need to include multiple chambers, and an optical detection apparatus may need to measure multiple chambers by scanning.

According to a conventional technique, in detection chambers of a lab-on-a-chip or lab-on-a-disk (a reactor), a reaction reagent in a dry state may be applied by test items. When blood is introduced, the reaction reagent may be melted, and generate a color reaction. Thus a density of analyte may be estimated using an optical density of a corresponding detection chamber. At this time, applying the reagent in the detection chamber may not be uniform depending on a location, and thus the color reaction may be various depending on the location. In addition, because the blood is introduced from one side, there may be differences in a melting rate of the reagent depending on the location, and this may also lead to differences in the location of the color reaction. An optical density may be various depending on a location of an inside of the detection chamber, and thus the density of analyte may be differently estimated when a measurement location is changed. Accordingly, mechanical dimensional tolerance of the lab-on-a-chip or lab-on-a-disk and mechanical misalignment between the optical detection apparatus and a cartridge mount may be reasons to reduce an accuracy and reproducibility of a test result.

In the exemplary embodiments, a test apparatus capable of measuring an optical density accurately and precisely regardless of an arrangement state of a lab-on-a-chip or a lab-on-a-disk cartridge, and a control method thereof, are provided.

Figure 2:
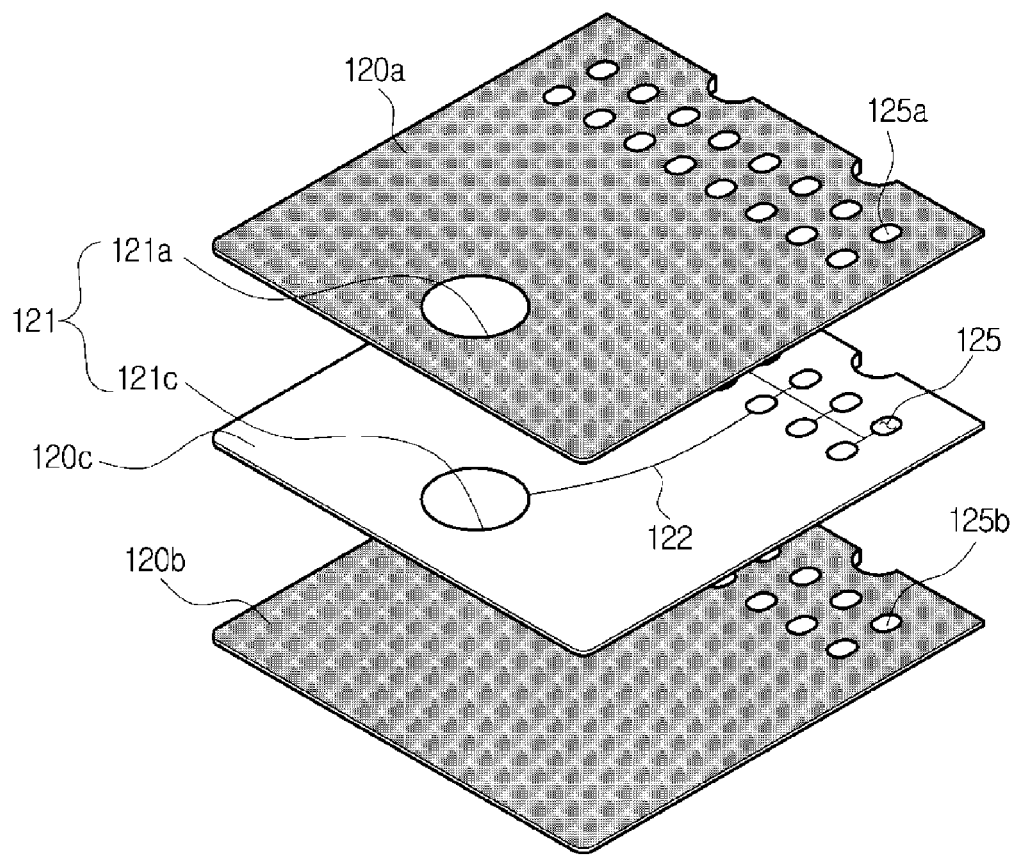
FIG. 2 is an exploded perspective view illustrating a structure of an inspector of the reactor of FIG. 1.

FIG. 1 is a view illustrating an exterior of a reactor 100 according to an exemplary embodiment. FIG. 2 is an exploded perspective view illustrating a structure of an inspector 120 of the reactor 100 of FIG. 1. The reactor may be, for example, a microfluidic device that is used to perform a reagent test method.

Referring to FIG. 1, the reactor 100 may be, for example, a microfluidic device in a type of a lab-on-a-chip, and is an analysis cartridge including a housing 110, a sample supplier 111, and the inspector 120 in which a reaction is generated by meeting a sample and a reagent. In another example, the reactor 100 may be a microfluidic device in a type of a lab-on-a-disk.

The housing 110 supports the inspector 120, and simultaneously allows a user to hold the reactor 100. The housing 110 may be formed of a material that is easily formed and that is chemically and biologically inactive. For example, the housing 110 may include one among various materials, including a plastic material, for example, acryl, such as polymethylmethacrylate (PMMA), polysiloxane, such as polydimethylsiloxane (PDMS), polycarbonate (PC), polyethylene, such as linear low density polyethylene (LLDPE), low density polyethylene (LDPE), medium density polyethylene (MDPE), and high density polyethylene (HDPE), polyvinylalcohol (PVA), very low density polyethylene (VLDPE), polypropylene (PP), acrylonitrile butadien styrene (ABS), and cyclo olefin copolymer (COC), glass, mica, silica, and a semiconductor wafer.

The sample supplier 111 in which the sample is supplied, is disposed on the housing 110. For example, the sample supplied to the reactor 100 may be one among various samples, including a bio sample, such as blood, tissue liquid, lymph liquid, urine, marrow fluid, and the like, and an environmental sample for water quality control and/or soil quality control. A target material subject to measurement of a density may be, for example, an electrolyte ion existing in the sample.

The inspector 120 may be attached to a lower portion of the housing 110 on which the sample supplier 111 is disposed, or may be inserted into a groove formed in the housing 110 so that the inspector 120 may be coupled to the housing 110.

Referring to FIG. 2, the sample supplied through the sample supplier 111, may be introduced into the inspector 120 through a sample inlet 121, and a filter may be disposed between the sample supplier 111 and the sample inlet 121 to filter the sample supplied through the sample supplier 111. For example, the filter may include one among a porous polymer membrane formed of polycarbonate (PC), polyethersulfone (PES), polyethylene (PE), polysulfone (PS), polyacrylsulfone (PASF), and the like. For example, when the sample is blood, the sample may be filtered such that blood cells are caught and only blood plasma or serum is introduced into an inside of the inspector 120.

The inspector 120 has a structure in which three plates are bonded to one another. The three plates include an upper plate 120a, a lower plate 120b, and a medium plate 120c disposed between the upper plate 120 and the lower plate 120b. The upper plate 120a and the lower plate 120b that are printed with a shielding ink protect the sample that is moved to a reagent chamber 125, from external light.

The upper plate 120a and the lower plate 120b may be formed of films, and the films used to form the upper plate 120a and the lower plate 120b may be selected from a polyethylene film, such as VLDPE, LLDPE, LDPE, MDPE, or HDPE, a PP film, a polyvinyl chloride (PVC) film, a PVA film, a polystyrene (PS) film, and a polyethylene terephthalate (PET) film.

The medium plate 120c of the inspector 120 may be formed of a porous sheet, such as cellulose, and the medium plate 120c itself may serve as a vent. The porous sheet may be formed of a material having hydrophobicity, or hydrophobic treatment may be performed on the porous sheet so that the porous sheet may not affect movement of the sample.

In the inspector 120, the sample inlet 121, a channel 122 in which the sample is moved, and the reagent chamber 125 in which a reaction of the sample and the reagent occurs, are provided. When the inspector 120 has a triple layer structure, an upper plate hole 121a of the sample inlet 121 is disposed in the upper plate 120a, and a portion 125a corresponding to the reagent chamber 125 is transparently disposed in the upper plate 120a.

Also, a portion 125b corresponding to the reagent chamber 125 is transparently disposed in the lower plate 120b. The portions 125a and 125b that correspond to the reagent chamber 125 may be transparently processed so that an optical property caused by the reaction that occurs in the reagent chamber 125 may be measured.

A medium plate hole 121c of the sample inlet 121 is disposed in the medium plate 120c, and when the upper plate 120a, the medium plate 120c, and the lower plate 120b are bonded to one another, the upper plate hole 121a and the medium plate hole 121c overlap each other so that the sample inlet 121 of the inspector 120 is formed.

Because the reagent chamber 125 is formed in an opposite region to the medium plate hole 121c among regions of the medium plate 120c, a portion of the opposite region is removed to form the reagent chamber 125 in a predetermined shape, such as a circular shape or a rectangular shape, and the upper plate 120a, the medium plate 120c, and the lower plate 120b may be bonded to one another so that the reagent chamber 125 is formed.

Also, the channel 122 having a width of 1 to 500 μm may be formed on the medium plate 120c so that the sample introduced through the sample inlet 121 may move up to the reagent chamber 125 due to a capillary force of the channel 122. However, the width of the channel 122 is merely an example that may be applied to the reactor 100, and exemplary embodiments are not limited thereto.

In the reagent chamber 125, a reagent to be used for the detection of the target material may be pre-accumulated. For example, a reagent configured to detect different items may be accumulated in a plurality of reagent chambers 125 and some of reagent chambers 125 may be blank chambers in which the reagent is not present.

As an example of pre-accumulating the reagent, each reagent in a fluid state may be applied on the portion 125a corresponding to the reagent chamber of the upper plate 120a or the portion 125b corresponding to the reagent chamber of the lower plate 120b, and dried. And then the upper plate 120a, the lower plate 120b, and the medium plate 120c may be bonded to one another so that the reagent may be accumulated in a dry state.

When the sample is supplied to the sample supplier 111 of the reactor 100, the supplied sample may be introduced into the inside of the inspector 120 through the sample inlet 121, and the introduced sample may be moved to each reagent chamber 125 along the channel 122.

Figure 3:
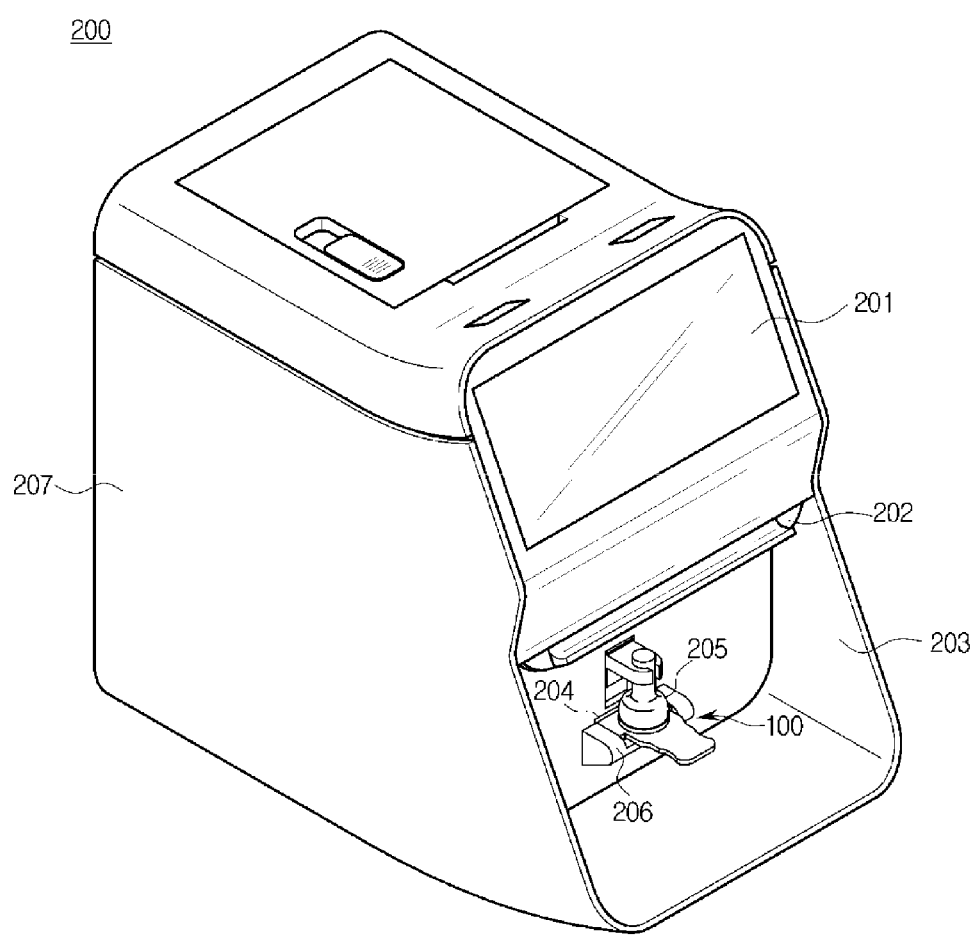
FIG. 3 is a view illustrating an exterior of a test apparatus according to an exemplary embodiment.

FIG. 3 is a view illustrating an exterior of a test apparatus 200 according to an exemplary embodiment. The test apparatus 200 is used to test the reactor 100.

The test apparatus 200 may be miniaturized and automated to inspect various samples, such as environmental samples, bio samples, food samples, and the like. For example, when using the test apparatus 200 for in vitro diagnosis of a bio sample collected from a human body, the in vitro diagnosis may be rapidly implemented in inspection rooms and other places, such as homes, offices, clinics, hospital rooms, emergency rooms, operating rooms, intensive care units, and the like, by users, including patients, doctors, nurses, medical laboratory technicians, and the like.

Referring to FIG. 3, the test apparatus 200 includes a mount 203 in which the reactor 100 is mounted, and when a door 202 of the mount 203 is slid upward to be opened, the reactor 100 is mounted on the test apparatus 200. As an example, the inspector 120 of the reactor 100 is inserted into a predetermined insertion groove 204 provided in the mount 203.

The inspector 120 of FIGS. 1 and 2 may be inserted into a main body 207, and the housing 110 of FIGS. 1 and 2 may be exposed to an outside of the test apparatus 200 and supported by a support 206. When a pressurizer 205 pressurizes the sample supplier 111 of FIGS. 1 and 2, the sample may be promoted to flow into an inside of the inspector 120.

After the sample is introduced into the inspector 120, the sample may be moved to the plurality of reagent chambers 125 via the channel 122 of FIG. 2, and the sample may react with the reagent in the reagent chamber 125 of FIG. 2.

When mounting of the reactor 100 is completed, the door 202 may be closed, and a test may be started. A light emitter 21 and a light receiver 22 (refer to FIG. 4) configured to measure an optical property and an electrical property, both of which vary depending on a density of a target material, may be provided in the main body 207. As an example of detecting an optical property, the light emitter 21 may emits light to the reagent chamber 125 in which the reagent is accumulated, and the light receiver 22 may detect light transmitted to the reagent chamber 125 or reflected from the reagent chamber 125. A user of the test apparatus 200 may control the test via an interface 201 of the test apparatus 200.

Figure 4:
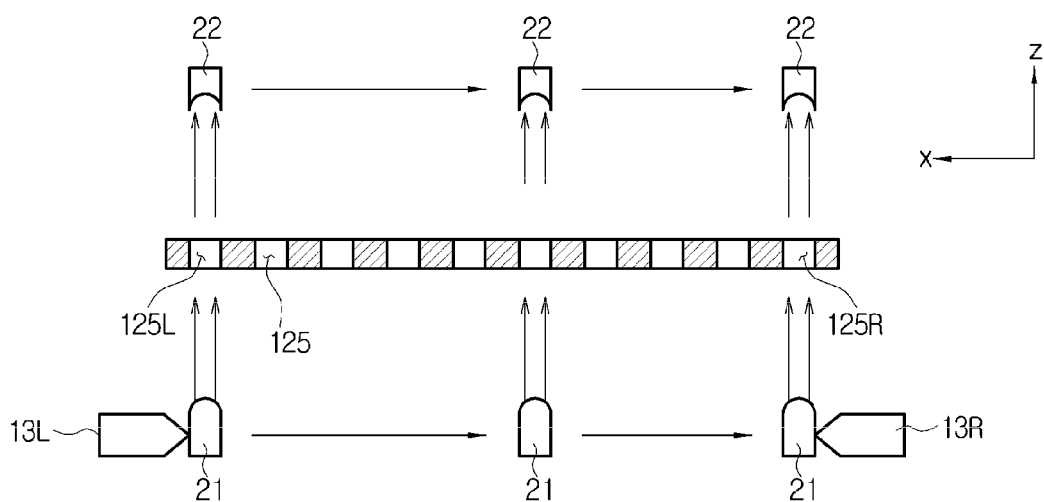
FIG. 4 is a schematic diagram illustrating a process of detecting a target object of a chamber by emitting light to the reactor according to an exemplary embodiment.

FIG. 4 is a schematic diagram illustrating a process of detecting a target object of the chamber 125 by emitting light to the reactor 100 according to an exemplary embodiment.

In FIG. 4, a cross-sectional view of the inspector 120 of the reactor 100 is illustrated. As illustrated in FIG. 4, the light emitter 21 emits light to a lower portion of the inspector 120, and the light receiver 22 receives light transmitted from the chamber 125 of the inspector 120.

The light emitter 21 and the light receiver 22 detect an optical density by emitting light to the chamber 125 of the inspector 120 while moving from a first hole 125L at a left side of the inspector 120 to a last hole 125R at a right side of the inspector 120.

A position sensor 13 of FIG. 6 described below may be disposed at the lower portion of the inspector 120 to detect whether the light emitter 21 and the light receiver 22 are placed in a reference position. As illustrated in FIG. 4, the position sensor 13 includes a first position sensor 13L and a second position sensor 13R that are disposed close to the first hole 125L and the last hole 125R of the inspector 120, respectively. The first position sensor 13L and the second position sensor 13R are illustrated, but when a position corresponding to the first hole 125L is referred to as a reference position, the second position sensor 13R installed to be close to the last hole 125R may be omitted.

According to a detection method, the position sensor 13 may output a detection signal to a processor 30 of FIG. 6 described below when the light emitter 21 and the light receiver 22 make contact with or are close to the position sensor 13. In addition, the position sensor 13 may prevent the light emitter 21 and the light receiver 22 from passing the reference position. That is, moving outside the reference position may be physically prevented by the position sensor 13.

A motor 82 of FIG. 6 described below may move the light emitter 21 and the light receiver 22. The light emitter 21 and the light receiver 22 may be moved from the left side to the right side or from the right side to the left side. The motor 82 may, for example, include a step motor.

Figure 5:
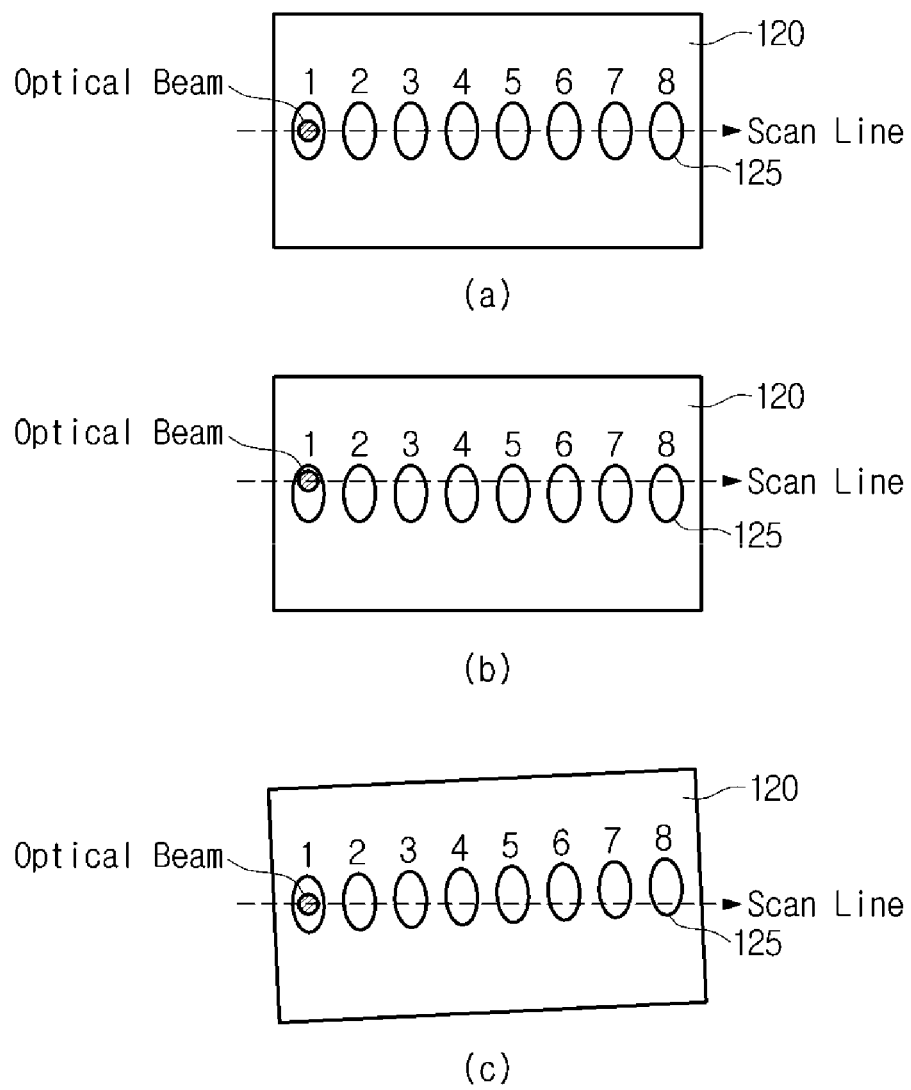
FIG. 5 is a schematic diagram illustrating an arrangement state of a scan line and the chamber when a light emitter and a light receiver scan the inspector according to an exemplary embodiment.

FIG. 5 is a schematic diagram illustrating a state of arrangement of a scan line and the chamber 125 when the light emitter 21 and the light receiver 22 scan the inspector 120 according to an exemplary embodiment.

As illustrated in FIG. 5, the inspector 120 of the reactor 100 includes eight (1 through 8) of the chambers 125. The inspector 120 may include, for example, 16 reagent chambers 125. A circle shape placed in the chamber 125 represents an optical beam emitted from the light emitter 21 disposed at the lower portion of the inspector 120, and FIG. 5 is a plane view looking down at the inspector 120 from above.

Portion (a) of FIG. 5 illustrates a correct arrangement state when the light emitter 21 and the light receiver 22 emit light and receive light, respectively, while scanning the chamber 125 of the inspector 120. That is, the light emitter 21 may emit light to the chamber 125 while scanning the inspector 120, and the light receiver 22 may receive light and measure an optical density while scanning the inspector 120. Portion (a) illustrates a case when the reactor 100 including the inspector 120 is placed in a proper position, i.e., in line with a scan line of the light emitter 21 and the light receiver 22. That is, the light emitter 21 and the light receiver 22 may scan a center line of the chamber 125 to measure the optical density of a center portion of the chamber 125.

Portions (b) and (c) illustrate an incorrect arrangement state when the light emitter 21 and the light receiver 22 emit light and receive light, respectively, while scanning the chamber 125 of the inspector 120. Portions (b) and (c) illustrate cases when the reactor 100 including the inspector 120 is installed not to be line with the scan line of the light emitter 21 and the light receiver 22. Accordingly, the optical density in a position of the chamber 125 intended to be measured may not be measured. Therefore, a difference in a result of measurement may occur, and an accuracy and a reproducibility of the test apparatus may be reduced.

Figure 6:
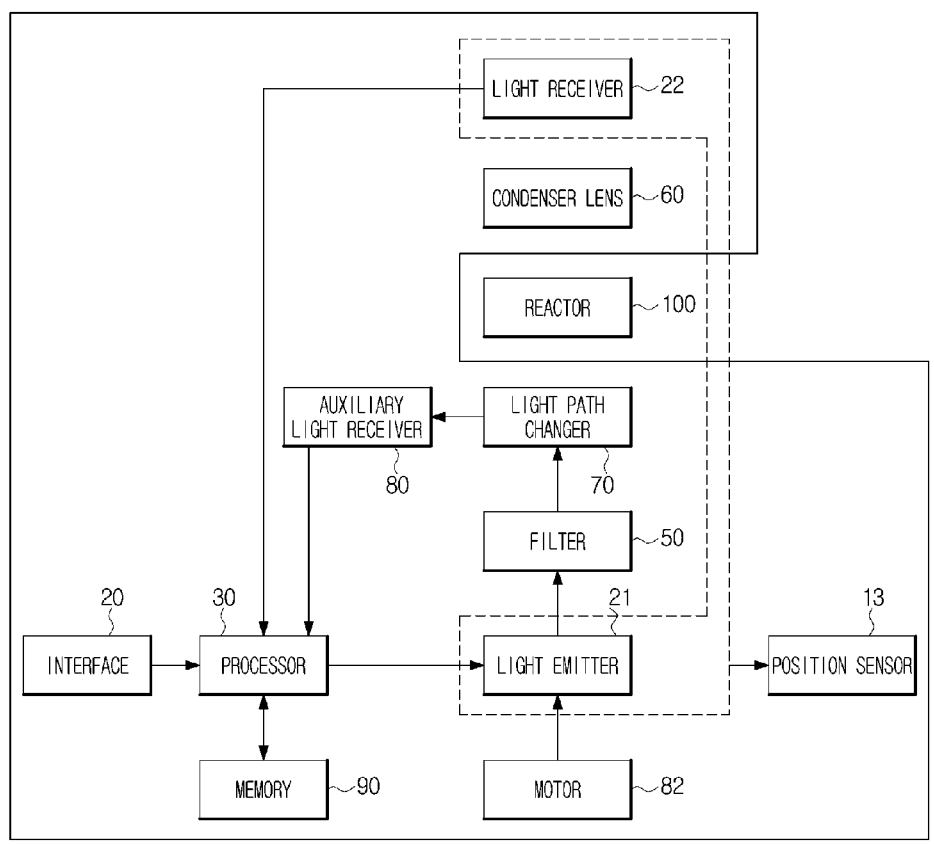
FIG. 6 is a block diagram illustrating a configuration of the test apparatus of FIG. 3.

FIG. 6 is a block diagram illustrating a configuration of the test apparatus 200 of FIG. 3.

As illustrated in FIG. 6, the test apparatus 200 includes an interface 20 receiving a command of a user from the outside, the light emitter 21 emitting light to the reactor 100, and the light receiver 22 detecting light that is emitted from the light emitter 21 and transmitted or reflected from the sample. The test apparatus 200 further includes the motor 82 supplying a power to move the light emitter 21 and the light receiver 22, the position sensor 13 detecting a location of the light emitter 21 and the light receiver 22, and the processor 30 controlling operations and functions of the test apparatus 200 according to commands inputted through the interface 20, and controlling operations of a control method of the test apparatus 200. In addition, the test apparatus 200 includes a filter 50 allowing light having predetermined wavelengths to be emitted to the reactor 100 among the light emitted from the light emitter 21, and a condenser lens 60 focusing light transmitted from the plurality of the chambers 125 of the reactor 100 toward the light receiver 22. In addition, the test apparatus 200 includes an auxiliary light receiver 80 receiving the light emitted from the light emitter 21 to measure variation of a strength of light emitted from the light emitter 21 and received by the light receiver 22, and a light path changer 70 changing a path of light to allow the auxiliary light receiver 80 to receive the light emitted from the light emitter 21. The test apparatus 200 further includes a memory 90.

As mentioned above, the reactor 100 is a device in which biochemical reaction occurs to determine the presence of a target material included in the sample, or to calculate a density of the target material, by receiving a biochemical sample, such as blood. The reactor 100 may include a reagent to detect the target material by reacting with the target material.

The light emitter 21 may include a planar light source having a great light emission area to uniformly emit light over an area of the reactor 100. For example, the light emitter 21 may be a backlight. In other examples, the light emitter 21 may be a light source to flick on and off at a predetermined wavelength, and may be any one among a semiconductor light emitter, such as a Light Emitting Diode (LED) or Laser Diode (LD), and a gas discharge lamp, such as a halogen lamp or xenon lamp.

The light receiver 22 detects light that is emitted from the light emitter 21 and that is transmitted or reflected from the sample placed in the chamber 125, and generates an electrical signal according to intensity of the light. The light receiver 22 may include, for example, a depletion layer photo diode, an avalanche photo diode, or a photomultiplier tube. In other examples, the light receiver 22 may include a complementary metal-oxide-semiconductor (CMOS) image sensor or a charge-coupled device (CCD) image sensor.

The light emitter 21 and the light receiver 22 may be disposed to face each other with respect to the reactor 100, or disposed on an upper portion of the reactor 100 and a lower portion of the reactor 100, respectively. According to the exemplary embodiments, the light emitter 21 and the light receiver 22 are disposed to face each other. The light emitter 21 and the light receiver 22 may be moved in a direction, in which the inspector 120 is arranged, to detect a result of reaction of the inspector 120. A power for the movement of the light emitter 21 and the light receiver 22 is supplied from the motor 82 of the test apparatus. The processor 30 controls driving of the motor 82 to control the movement of the light emitter 21 and the light receiver 22.

The intensity and wavelengths of light emitted from the light emitter 21 are controlled by a command from the processor 30. The light receiver 22 sends an electrical signal generated by detecting light to the processor 30. The light emitter 21 and the light receiver 22 may further include an AD converter configured to convert a detection result of the light receiver 22 into a digital signal and output the digital signal to the processor 30.

A display unit of the test apparatus 200 may display a test result. As illustrated in FIG. 6, the inspector 120 of the reactor 100 includes the plurality of chambers 125 so that a plurality of test items may be detected from the single reactor 100. When the plurality of test items are detected, the display unit may display test results of the plurality of test items.

The interface 20 is used to input information related to operations of the test apparatus 200.

The processor 30 controls operations of a control method of the test apparatus 200.

The filter 50 may be mounted to the light emitter 21, and detects light having predetermined wavelengths among light emitted from the light emitter 21. By emitting the light having the predetermined wavelengths detected by the filter 50 to the chamber 125 of the inspector 120, differences in light wavelengths emitted from the light emitter 21 between a plurality of the test apparatuses 200 may be reduced. A detailed description of the filter 50 will be described with reference with FIG. 15.

The condenser lens 60 is disposed between the reactor 100 and the light receiver 22, and focuses light transmitted from the plurality of chamber 125 of the inspector 120 to be received at the light receiver 22 in which an area is smaller than that of the inspector 120. A detailed description of the condenser lens 60 will be described with reference with FIG. 17.

The auxiliary light receiver 80 measures variation of reduction of the intensity of light emitted from the light emitter 21 while the light receiver 22 scans the plurality of the chamber 125 of the inspector 120. The auxiliary light receiver 80 receives light emitted from the light emitter 21 to compensate for an amount of reduced intensity of light. The light path changer 70 changes a path of light so that the auxiliary light receiver 80 receives light emitted from the light emitter 21. A detailed description of the auxiliary light receiver 80 and the light path changer 70 will be described with reference with FIG. 18.

Figure 7:
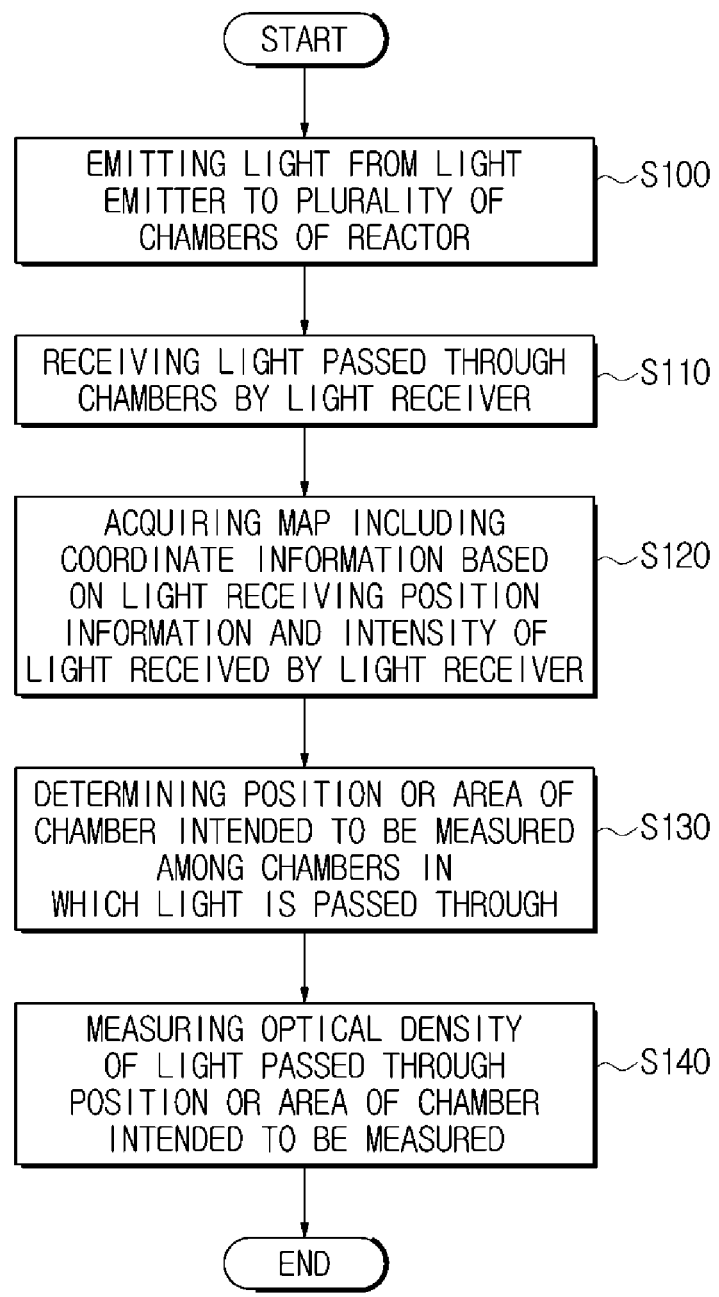
FIG. 7 is a flow chart illustrating a control method of a test apparatus according to an exemplary embodiment.

FIG. 7 is a flow chart illustrating a control method of a test apparatus according to an exemplary embodiment.

Hereinafter, a test apparatus and a control method thereof according to exemplary embodiments will be described with reference with FIGS. 6 to 19.

As illustrated in FIG. 7, in operation S100, the control method includes emitting light from the light emitter 21 to the plurality of chambers 125 disposed in the inspector 120 of the reactor 100.

In operation S110, the control method includes receiving light passed through the chambers 125 by the light receiver 22.

In operation S120, the control method includes acquiring an optical density map including coordinate information based on light receiving position information and an intensity of the light received by the light receiver 22.

In operation S130, the control method includes determining a position or an area of the chamber 125 intended to be measured among the chambers in which the light is passed through, based on the optical density map.

In operation S140, the control method includes measuring an optical density of light that passes through the position or the area of the chamber 125 intended to be measured.

Figure 8:
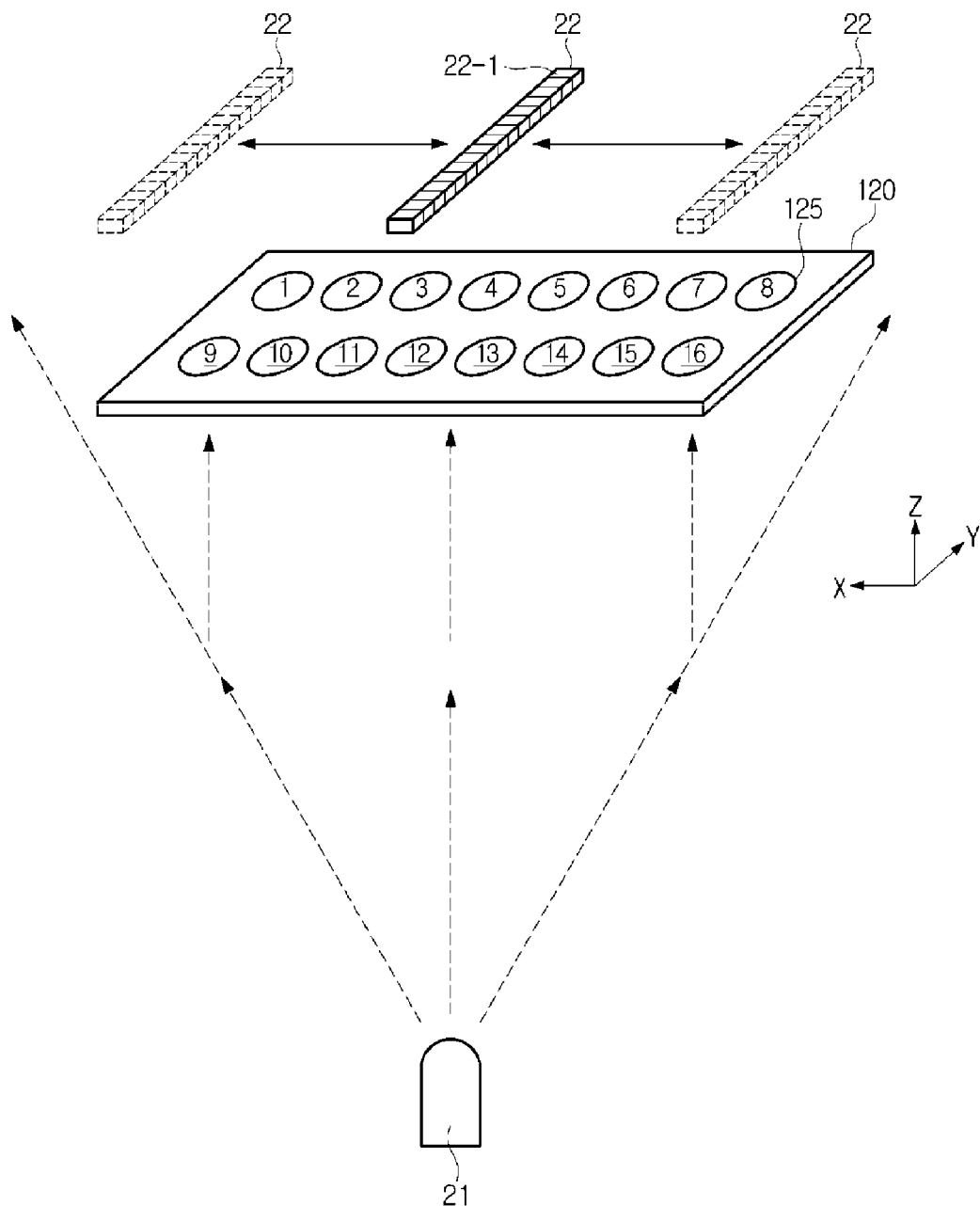
FIG. 8 is a schematic diagram illustrating operations of a test apparatus according to an exemplary embodiment.

FIG. 8 is a schematic diagram illustrating operations of a test apparatus according to an exemplary embodiment.

As illustrated in FIG. 8, the chambers 125 included in the inspector 120 of the reaction unit 100, includes 16 chambers. In each of the chambers 125, a reagent may be applied in a dry state by a test item. The reagent may be melted, and occur a color reaction when a sample, such as blood, is introduced. To analyze material, such as blood, an optical density of light transmitted through the chambers 125 is measured.

The light emitter 21 is disposed at a lower portion of the inspector 120, and emits light to the chambers 125. As mentioned in FIG. 4, the light emitter 21 may emit light while moving along an arrangement of the chambers 125, but according to FIG. 8, the light emitter 21 emits light while being fixed. When the light emitter 21 is fixed, to emit light to all of the chambers 125, a distance between the inspector 120 and the light emitter 21 may be further than that of a conventional case. When the distance between the inspector 120 and the light emitter 21 is further, light introduced into the chamber 125 may be introduced in a direction perpendicular to the chamber 125. That is, light introduced into the chamber and light introduced to chambers ① to ⑨ may be introduced in a direction perpendicular to the inspector 120.

The light receiver 22 receives light emitted from the light emitter 21 and transmitted through the chambers 125. As illustrated in FIG. 8, the light receiver 22 is formed in a photodiode array in which light receiving elements 22-1 corresponding to one or more pixels are arranged. That is, at least one of the light receiving elements 22-1 independently receives light, and the receiving light elements 22-1 are arranged in an array so that the light receiver 22 receives the light introduced through the chambers 125 in a direction in which the light receiving elements 22-1 are arranged while scanning the inspector 120.

Referring to FIG. 8, the light receiver 22 is disposed at an upper portion of the inspector 120, and scans the inspector 120 while moving in an array direction of the chambers 125. The array direction of the chambers 125 as illustrated in FIG. 8 is a left or right direction, and the light receiver 22 may be moved from a left side to a right side or from the right side to the left side. The light receiver 22 receives the light transmitted through the chamber 125 while scanning the inspector 120, and sends information related to the received light to the processor 30. For example, the information related to the received light may include a light receiving position and an intensity of the light according to a scan position of the light receiving elements 22-1.

Figure 9:
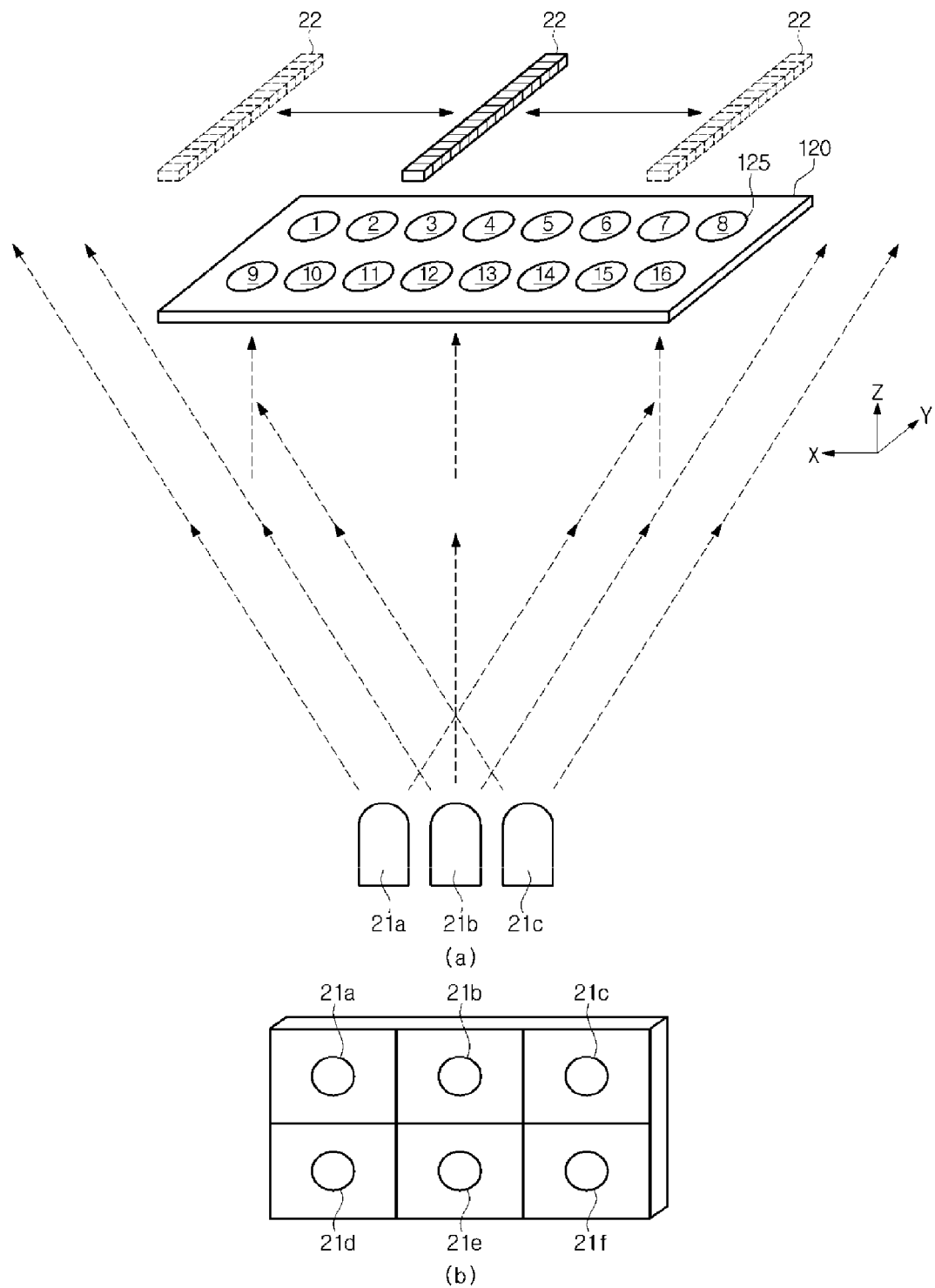
FIG. 9 is a view illustrating a plurality of light emitters and a schematic diagram illustrating operations of a test apparatus including the plurality of light emitters according to an exemplary embodiment.

FIG. 9 is a view illustrating a plurality of light emitters and a schematic diagram illustrating operations of a test apparatus including the plurality of light emitters according to an exemplary embodiment.

As illustrated in portion (a) of FIG. 9, the test apparatus 200 includes a plurality of light emitters 21a, 21b, and 21c, and the plurality of light emitters emit light. A number of the plurality of light emitters and an array type of the plurality of light emitters are not limited. The exemplary embodiment illustrated in portions (a) and (b) of FIG. 9 is an example.

Portion (b) of FIG. 9 is a plane schematic view looking down at the plurality of light emitters 21a, 21b, and 21c as arranged, from above. The plurality of light emitters 21a, 21b, and 21c may include light sources emitting different wavelengths from each other, and may include, for example, any one among a semiconductor light emitter, such as a Light Emitting Diode (LED) or Laser Diode (LD), and a gas discharge lamp, such as a halogen lamp or xenon lamp. The test apparatus 200 may further include a plurality of light emitters 21d, 21e, and 21f that emit light.

As illustrated in the portion (a) of FIG. 9, because the plurality of light emitters 21a, 21b, and 21c are disposed to be far from the inspector 120, the light emitted to the inspector 120 is emitted in a direction perpendicular to the inspector 120. That is, as illustrated in the portion (b) of FIG. 9, the plurality of light emitters 21a, 21b, and 21c are disposed at an interval of a distance. The plurality of light emitters 21a, 21b, and 21c may be flashed on and off depending on predetermined wavelengths. That is, each of the light emitters 21a, 21b, and 21c may be selectively controlled to emit the light having a predetermined wavelength including an optical density intended to be measured, to the chambers 125 of the inspector 120. A command related to the light emitter(s) intended to emit light may be inputted through the interface 20, and the processor 30 may emit light by controlling the light emitter(s) based on the inputted command.

As illustrated in the portion (a) of FIG. 9, each of the light emitters 21a, 21b, and 21c emit light to all of the chambers 125, as illustrated in FIG. 8. By using the light emitters 21a, 21b, and 21c emitting the light of different wavelengths, an optical density may be measured depending on each wavelength, and a map including coordinate information of positions of the chambers 125 corresponding to each wavelength may be acquired.

Figure 10:
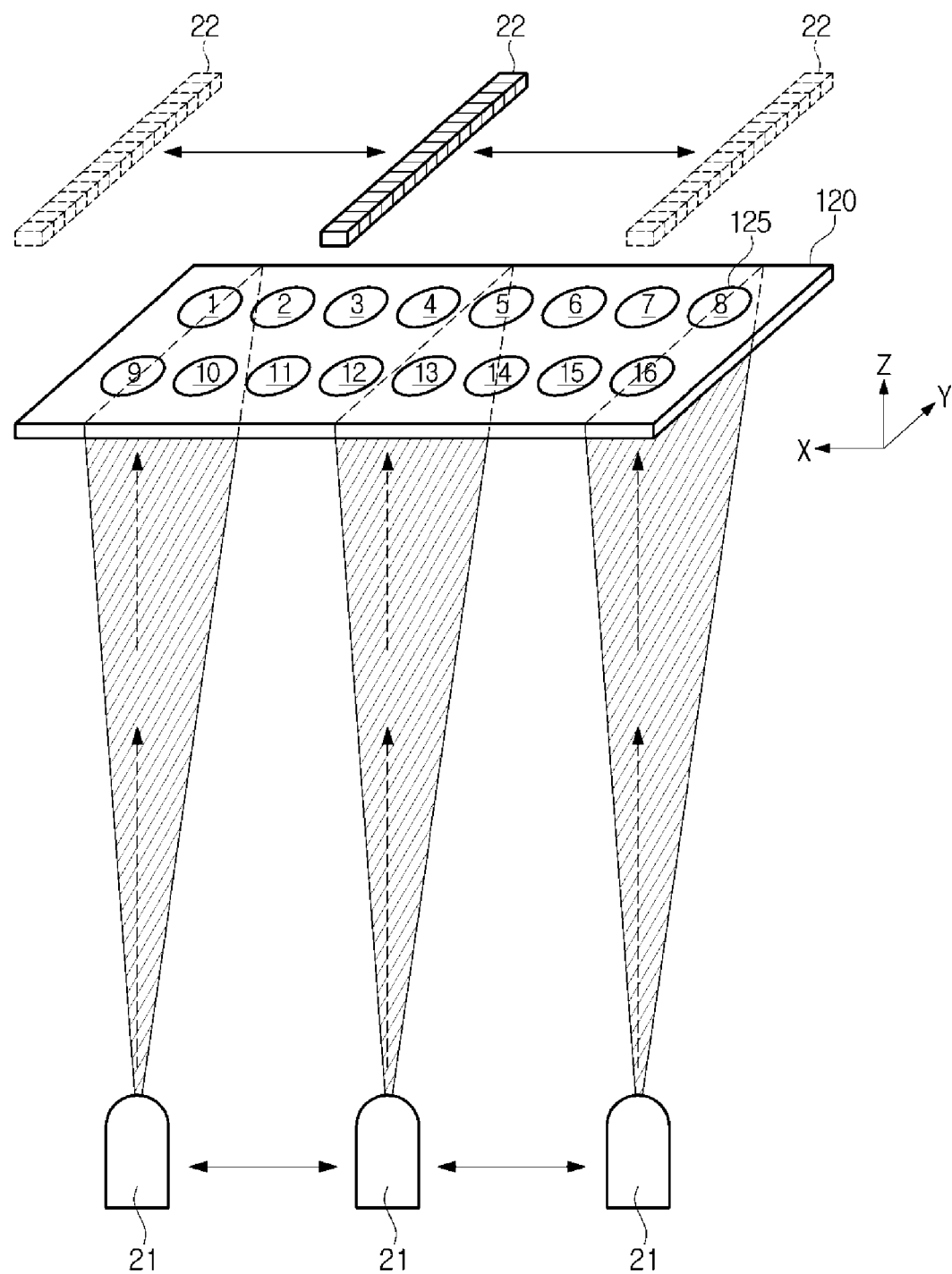
FIG. 10 is a schematic diagram illustrating operations of a test apparatus in which a light emitter emits light while scanning an inspector by corresponding to a light receiver according to an exemplary embodiment.

FIG. 10 is a schematic diagram illustrating operations of a test apparatus in which a light emitter emits light while scanning an inspector by corresponding to a light receiver according to an exemplary embodiment.

As illustrated in FIG. 10, the light emitter 21 emits light while moving in a direction in which the light emitter 21 scans the inspector 120. When the light emitter 21 emits light, the light receiver 22 receives light through the chambers 125. The light emitter 21 and the light receiver 22 move in a scan direction of the inspector 120.

For example, when the light emitter 21 is disposed in a last left position, the light emitter 21 emits light to a chamber ① and a chamber ⑨. Light passed through the chambers is received in the light receiver 22 placed in the last left position. When the light emitter 21 is disposed in a center position, the light emitter 21 emits light to a chamber ④ and a chamber ⑫, and the light receiver 22 placed in the same center position as the light emitter 21 receives light. When the light emitter 21 emits light while scanning the inspector 120 to correspond to the light receiver 22, the light emitter 21 emits light to only the corresponding chamber 125 so that the light receiver 22 receives light according to a corresponding position of the light receiver 22 without emitting light to an entire area of the chambers 125. That is, in FIG. 10, when the light emitter 21 is disposed in the last left position, the light receiver 22 corresponding to the light emitter 21 is also disposed in the last left position. Therefore, the light emitter 21 emits light to the chamber ① and the chamber ⑨.

In FIG. 10, because the light receiver 22 is formed in an array, all of light passed through the chambers 125 in a Y-axis direction of the inspector 120 is received. Therefore, the light emitter 21 emits light to pass through the chambers 125 in the Y-axis direction, such as the chamber ① and the chamber ⑨.

But if the light receiver 22 is formed by the light receiving element 22-1 not formed in an array, the light receiver 22 may scan an entire area of the inspector 120 in an X-axis or Y-axis direction. In this example, light emitted from the light emitter 21 may pass through a single chamber 125.

Figure 11A:
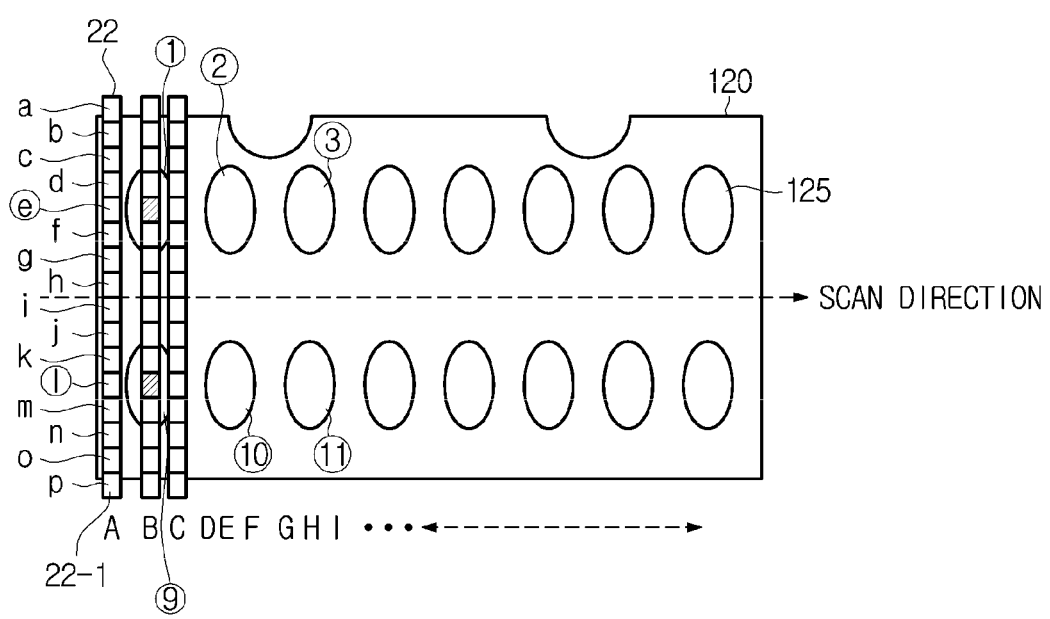
FIG. 11A is a conceptual diagram illustrating a method of determining a position or an area of a plurality of chambers through which light penetrates according to an exemplary embodiment.

FIG. 11A is a conceptual diagram illustrating a method of determining a position or an area of a plurality of chambers through which light penetrates according to an exemplary embodiment.

FIG. 11A is a plane view illustrating the light receiver 22 receiving light emitted from the light emitter 21 while scanning the chambers 125 of an inspector 120. The light receiver 22 includes the light receiving elements 22-1 of a size and arranged in a row. However, an arrangement type of the light receiving elements 22-1 and a shape of the light receiver 22 may vary. When scanning the inspector 120, the light receiver 22 is disposed on or over the chambers 125 or outside of the chambers 125. Positions of the light receiver 22 may be represented by A, B, C, and D according to a scan direction of the light receiver 22, but may vary according to the light receiving type of the light receiver 22. The light receiver 22 may receive light emitted from the light emitter 21 while scanning each position of the inspector 120 also represented by A, B, C, and D. In addition, the light receiver 22 may be formed in a photodiode array in which the light receiving elements 22-1 corresponding to one or more pixels are arranged, and the one or more pixels corresponding to each of the light receiving elements 22-1 may be represented as a number a to a number p. That is, the light receiving elements 22-1 corresponding to a pixel a to a pixel p included in the light receiver 22 receive light emitted from the light emitter and passed through the chambers 125. Therefore, the light receiver 22 may acquire information related to which pixel receives light at which position in a scan direction, and may transmit the information to the processor 30.

FIG. 11B a graph illustrating that a light receiver acquires information related to a light receiving position of light and an intensity of light by receiving light according to an exemplary embodiment.

As illustrated in FIG. 11B, an X-axis represents pixel numbers corresponding to the light receiving elements 22-1 included in the light receiver 22, as illustrated in FIG. 11A, and a Y-axis represents an intensity of light that is received by the light receiver 22. In addition, a curve displayed on coordinates represents an intensity of light received by the light receiving elements 22-1 according to a scan direction in which the light receiver 22 scans. In FIG. 11B, cases when chambers ①and ⑨, chambers ③and ⑩, and chambers ③and ⑪ receive light are described, but other chambers may be illustrated as a graph in the same coordinates. Hereinafter, the case when light received in the chamber ① and the chamber ⑨ is illustrated as a graph will be described as an example.

Referring to FIG. 11A, the light receiver 22 may be placed in A, B or C position during scanning the chamber ① and the chamber ⑨. When the light receiver is placed in the A position, all of the light receiving elements 22-1 of the light receiver 22 are not placed in the chamber ① and the chamber ⑨ so that the light receiver 22 do not receive light emitted from the light emitter 21. An intensity of light is described to be about 0 as a curve A on a graph of the chamber ① and the chamber ⑨ in FIG. 11B. Rectangle shapes having an array shape illustrated along the X-axis represent pixels forming the light receiver 22.

When the light receiver 22 is placed in the B position, adjacent light receiving elements including $e^{th}$ and $l^{th}$ pixels are placed in the chamber ① and the chamber ⑨. Therefore, the largest amount of light emitted from the light emitter 21 is received. An intensity of light of the B position, such as a B curve on a graph of the chamber ① and the chamber ⑨ FIG. 11B, is displayed to be the highest among that of A and C position. When placed in the B position, an intensity of received light varies according to positions of the light receiving elements included in the light receiver 22. That is, on the graph of the chamber ① and the chamber ⑨, the largest amount of light is received in the $e^{th}$ and $l^{th}$ pixel, and thus the light intensity in the $e^{th}$ and $l^{th}$ pixel are displayed to be the highest.

When the light receiver 22 is placed in the C position, adjacent light receiving elements including $e^{th}$ and $l^{th}$ pixel are disposed at a position where a part of the chamber ① and the chamber ⑨ is included. Therefore, a part of light emitted from the light emitter 21 is received. As illustrated in a C curve on the graph of the chamber ① and the chamber ⑨ in FIG. 11B, pixels of the light receiver 22, such as $a^{th'}$ and $b^{th}$ pixel rarely receive light, and the $e^{th}$ and $l^{th}$ pixel receive a portion of light. Therefore, an intensity of light in the $e^{th}$ and $l^{th}$ pixel is displayed to be weaker on the C curve than on the B curve.

Accordingly, while the light receiver 22 scans the chambers 125, the light receiver 22 acquires coordinate information that is an amount of light received on which position of which number chamber 125, by using information related to light receiving positions of pixels configured to receive light, and information related to an intensity of light according to the light receiving position.

FIG. 12 is a schematic diagram of a map illustrating information related to a light receiving position and an intensity of received light in a coordinate system according to an exemplary embodiment.

Portion (a) of FIG. 12 illustrates a map of a case when a scan direction of the light receiver 22 and an arrangement state of the chamber 125 of the inspector 120 are matched. Portion (b) of FIG. 12 illustrates a map of a case when a scan direction of the light receiver 22 and an arrangement state of the chamber 125 of the inspector 120 are not matched. The processor 30 may determine a position or an area of the plurality of chamber in which light is penetrated by the process, as illustrated in FIG. 11A, based on received information from the light receiver 22. The processor 30 may acquire a map in which information related to the light receiving position of light received by the light receiver 22, and information related to an intensity of light are represented by coordinate information.

As illustrated in FIG. 11A, light received by the light receiver 22 may correspond to light received by each pixel corresponding to the plurality of light receiving elements so that the light received by the light receiver 22 may be displayed by coordinate values in all positions of the chamber 125. FIG. 12 illustrates a case when information related to light received in the center of the chamber 125 is displayed by coordinates. As illustrated in portion (a) of FIG. 12, when a scan direction of the light receiver 22 and an arrangement state of the chamber 125 of the inspector 120 are matched, the chamber ① and the chamber ⑨, as illustrated in FIG. 11A, may be in a scan direction, the light receiver 22 may be placed in the B position, and thus information related to light receiving elements of the $e^{th}$ and $l^{th}$ pixel receiving the largest amount of light may be displayed by coordinate information, such as (B, e) and (B, l). The processor 30 may store acquired coordinate information in the memory 90. Therefore, as for a detection of light, information of the center portion of all of the chambers 125 may be acquired by coordinates information. By using this, although an arrangement state of the inspector 120 is not matched, it may be recognized which position corresponds to a center portion of the chamber 125, and an optical density of the position may be measured.

As illustrated in portion (b) of FIG. 12, when a scan direction of the light receiver 22 and an arrangement state of the chamber 125 of the inspector 120 are not matched, information related to the center portion of all of the chambers 125 may be stored as coordinate information.

Referring to FIG. 7 again, based on the map illustrated in FIG. 12, the processor 30 may determine a position and an area of the chamber intended to be measured among the plurality of the chamber 125 in which light emitted from the light emitter 21 is passed through (operation S130). Based on the coordinate information of the map acquired at operation S120, the position and area of the chamber 125 in which light is emitted may be determined. The position and area of the chamber 125 may correspond to a position or an area or an adjacent area of a position or an area of the chamber. That is, the processor 30 may determine the position and area of the chamber 125 intended to be measured.

Based on the position and area of the chamber 125 determined at operation S130, the processor 30 may measure an optical density of light passed through the position or area of the chamber 125 intended to be measured (operation S140). As illustrated in FIGS. 11A, 11B, and 12, in order to acquire an optical density of the center portion of the chamber 125, a map related to coordinates of the center portion may be acquired, and based on the map including the coordinates, the optical density of the center portion of the chamber 125 may be acquired even when an arrangement state of the inspector 120 are not matched. When measuring the optical density on the center portion of the chamber 125, an optical density passed through the exact center portion may be acquired by using coordinates value of the exact center portion.

An optical density may be derived from an average value by measuring an optical density in adjacent position within a distance from the center portion. That is, when the optical density in the center portion is not measured or when a difference generated in the optical density of the center portion is need to be compensated, an average value of the optical density in the adjacent position may be used. At this time, in order to measure an optical density based on the average value, data relate to deriving an average value based on an optical density of how distant regions from the central portion to measure the optical density from the average value may be pre-stored in the memory 90. In addition, the processor 30 may determine an area in which measuring optical density is affected by bubbles or foreign material existing in the chamber 125 based on a map for measuring optical density, and the processor 30 may exclude the area when measuring an average optical density. The area including bubbles or foreign material may be inputted through the interface 20, or may be stored in the memory 90.

Figure 13:
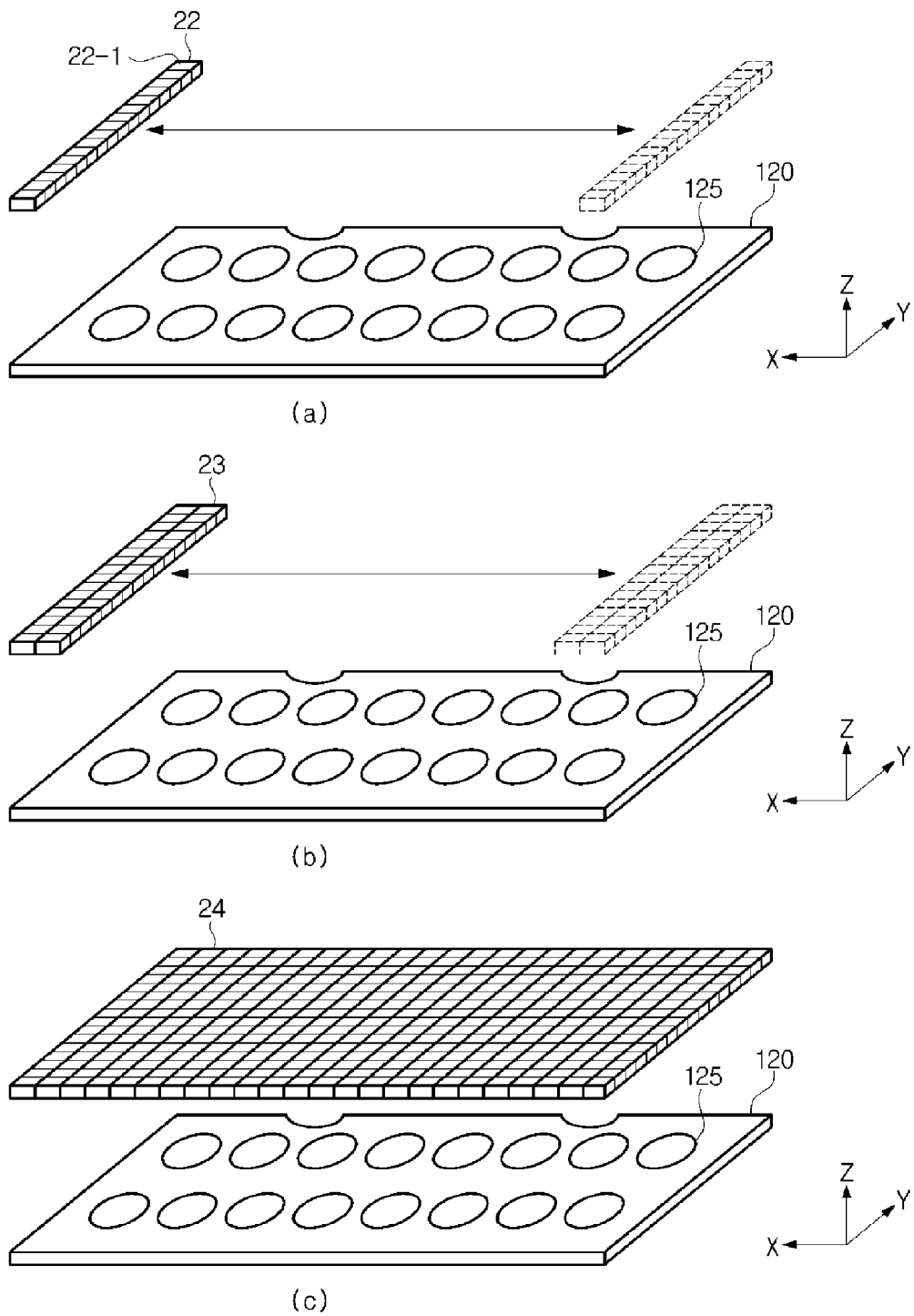
FIG. 13 is a view illustrating various shapes of a light receiver according to an exemplary embodiment.

FIG. 13 is a view illustrating various shapes of a light receiver according to an exemplary embodiment.

The light receiver 22 illustrated in portion (a) of FIG. 13 may be formed in a photodiode array in which light receiving elements 22-1 corresponding to at least one pixel are arranged, as illustrated in FIG. 8. That is, the plurality of receiving light elements 22-1 may be arranged in an array so that the light receiver 22 may receive light introduced through the chamber 125 in a direction in which receiving light elements are arranged while scanning the inspector 120.

A light receiver 23 illustrated in portion (b) of FIG. 13 may be the plurality of receiving light elements arranged in two dimensional array. Unlike as illustrated in portion (a) of FIG. 13, the light receiving elements is arranged in two lines to form the light receiver 23. When scanning the chamber 125, light may be received by using a larger area of the light receiver 23. Therefore, in portion (a) of FIG. 13, the light receiver 22 including a single line may scan the chamber 125, but in portion (b) of FIG. 13, the light receiver 23 including two lines may scan the chamber 125 while moving by per area including two lines. Accordingly, a scan speed of the light receiver 23 may be faster than that of the light receiver 22.

A light receiver 24 illustrated in portion (c) of FIG. 13 may be the plurality of light receiving elements arranged in two dimensional array, that is, the light receiver 24 may have an area equal to or larger than the inspector 120. When the light receiver 24 has an area equal to or larger than the inspector 120, the chamber 125 may not need to scan the inspector 120 to receive light passed through the chamber 125. Thus, a map including coordinates information of position of the chamber may be acquired by receiving light without physical scan motion.

As illustrated in FIG. 13, the light receivers 22, 23, and 24 may have various shapes. The light receiver 23 including two lines may have a faster scan speed than the light receiver 22 including one line. As an area of the light receiver is larger, receiving light may be performed by less scan motion, and thus a scan speed may be faster. However, as an area of the light receiver is larger, the production cost may be increased, and thus the light receiver may be selected while considering a scan speed and the production cost.

FIG. 14 is a view illustrating a direction in which a light receiver scans an inspector according to an exemplary embodiment.

As illustrated in FIG. 14, light receivers 22 and 25 may scan the inspector 120 in various directions, and a scan direction may vary according to a shape of the light receiver. Portion (a) of FIG. 14 illustrates that the light receiver 22 scans in a X-axis direction of the inspector 120. Portion (b) of FIG. 14 illustrates that the light receiver 25 scans in a Y-axis direction of the inspector 120.

FIG. 14 illustrates scanning in X- or Y-axes directions, but is not limited thereto. The light receiver 22 of portion (a) may have light receiving elements arranged in array with a length of Y-axis of the inspector 120, and the light receiver 25 of portion (b) may have light receiving elements arranged in array with a length of X-axis of the inspector 120. The light receiver 22 of portion (a) may receive light passed through the chamber 125 arranged in Y-axis of the inspector 120 while scanning the inspector 120, and the light receiver 25 of portion (b) may receive light passed through the chamber 125 arranged in X-axis of the inspector 120 while scanning the inspector 120. Accordingly, a scan direction and a scan speed of scanning the inspector 120 may be various according to a shape of light receiving elements. In addition, scanned chamber 125 may be various, and thus a graph shape illustrated in FIG. 11B, and a map shape illustrated in FIG. 12 may be various.

Figure 15:
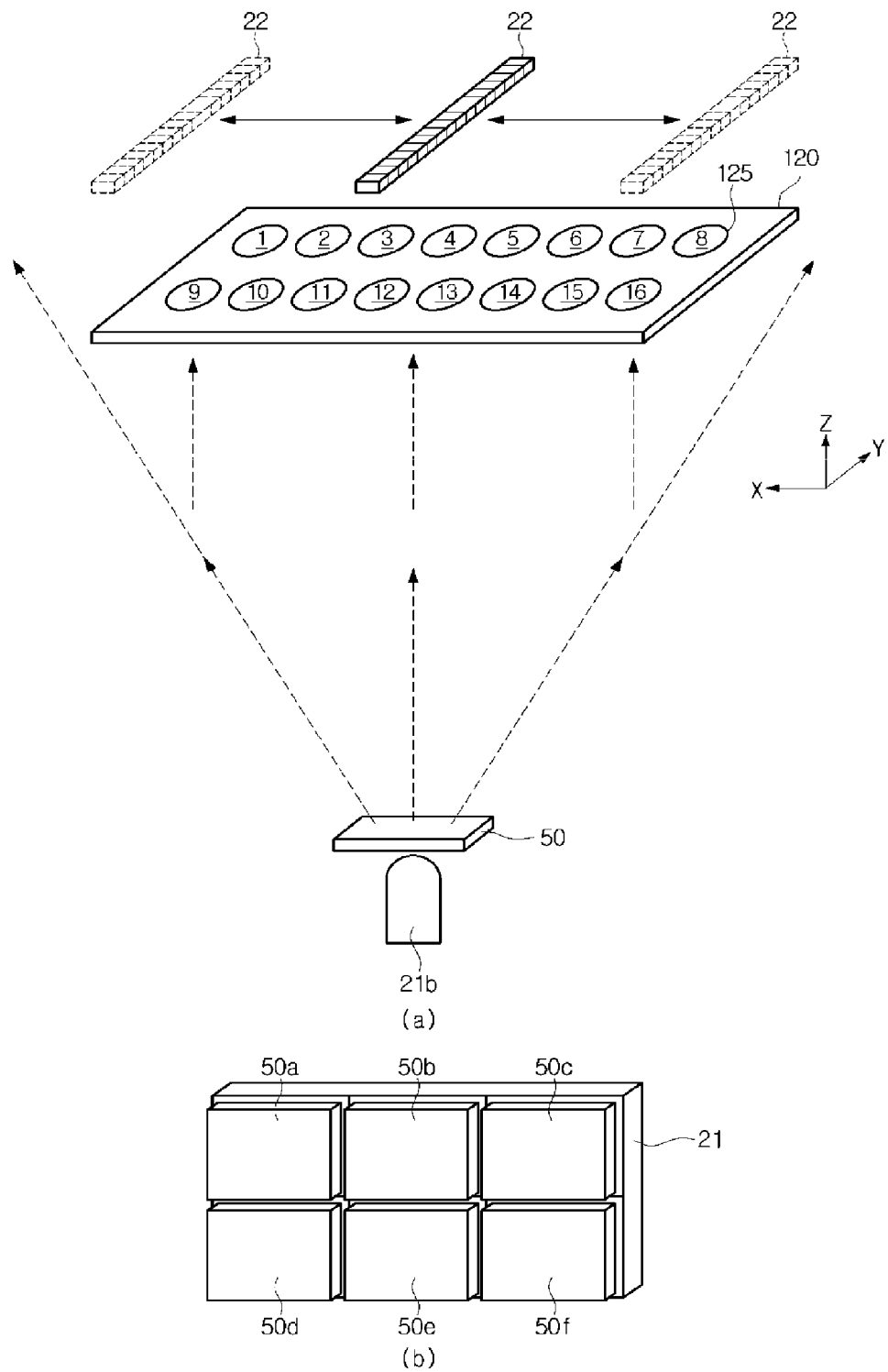
FIG. 15 is a schematic diagram illustrating operations of a test apparatus including a filter and a view illustrating a filter installed in a light emitter according to an exemplary embodiment.
Figure 16:
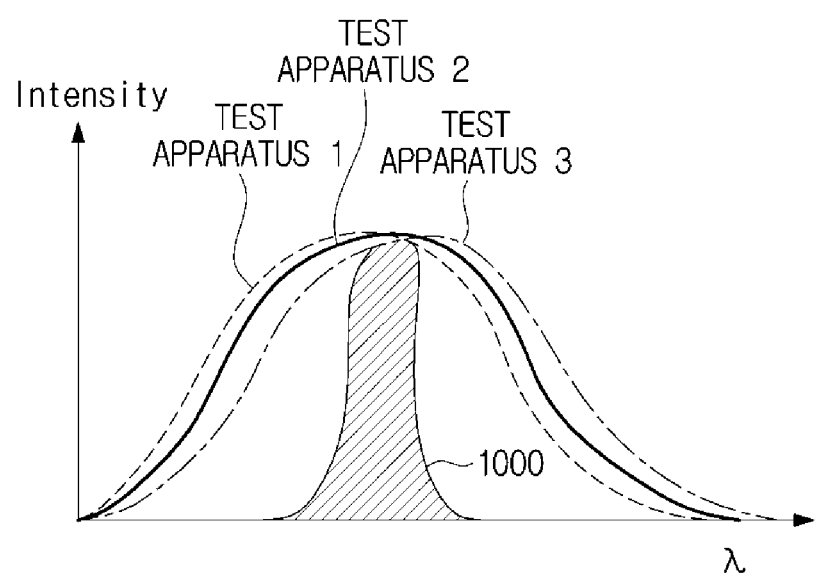
FIG. 16 is a graph illustrating a result of operations of a test apparatus when the test apparatus includes a filter according to an exemplary embodiment.

FIG. 15 is a schematic diagram illustrating operations of a test apparatus including a filter and a view illustrating a filter installed in a light emitter according to an exemplary embodiment. FIG. 16 is a graph illustrating a result of operations of a test apparatus when the test apparatus includes a filter according to an exemplary embodiment.

As illustrated in portion (a) of FIG. 15, the filter 50 may be disposed adjacent to the light emitter 21b. The filter 50 may detect light having predetermined wavelengths among light emitted from the light emitter 21b. When emitting light having wavelengths detected by the filter 50 to the inspector 120, the light receiver 22 may receive light passed through the chamber 125. Operations of the test apparatus 200 which the light receiver 22 receives light by emitting light to the light emitter 21 is illustrated in FIG. 8, and thus a duplicate description will be omitted.

The filter 50 may employ a band pass filter configured to detect light having predetermined wavelengths among light emitted from the light emitter 21, and may be formed of glass or plastic. The kind of the filter may be various according to the kind of wavelengths intended to be detected, and the material of the filter may be not limited thereto. A user may input information through the interface 20 wherein the information is related to wavelengths intended to be detected. The processor 30 may detect wavelengths by controlling the filter 50 based on information of wavelengths pre-stored in the memory 90.

Portion (b) of FIG. 15 is a view illustrating that each of the plurality of light emitters of FIG. 9 include a plurality of filters 50a, 50b, 50c, 50d, 50e and 50f. There is no limit to the number and array type of the plurality of filters. The plurality of filter may be installed in the plurality of light emitters, or a single filter may be installed in the plurality of light emitters. As the plurality of light emitters may emit light having predetermined wavelengths, the plurality of filters may be included in the test apparatus 200 to detect light having wavelengths among light emitted from the light emitter. In the test apparatus 200, a distance between the light emitter 21 and the inspector 120 may be longer so that a distance between the plurality of light emitters may be wider also. Therefore, the filter 50 may be installed adjacent to the light emitter.

Because the wavelengths may be different even when wavelengths emitted by the light emitter 21 included in each test apparatus 200 are set to be the same, a result may be various according to the type of test apparatus. Accordingly, a reason of installing the filter 50 may prevent the result from being various.

An X-axis of FIG. 16 may represent a wavelength range of light emitted from test apparatuses, and Y-axis may represent an intensity of light. Even when each test apparatus is set to emit light having the same wavelengths, a range of wavelengths emitted from a light emitter of test apparatus 1 and test apparatus 3 may be different to each other, as illustrated in FIG. 16. Therefore, by installing the filter 50, a range of wavelengths 1000 may be selected within a range of the wavelength of the light emitted from the test apparatus 1 and the test apparatus 3 so that light having the same wavelengths 1000 may be emitted from the test apparatus 1 and the test apparatus 3. The filter 50 may be installed so that differences, which may be generated according to apparatuses, may be reduced.

Figure 17:
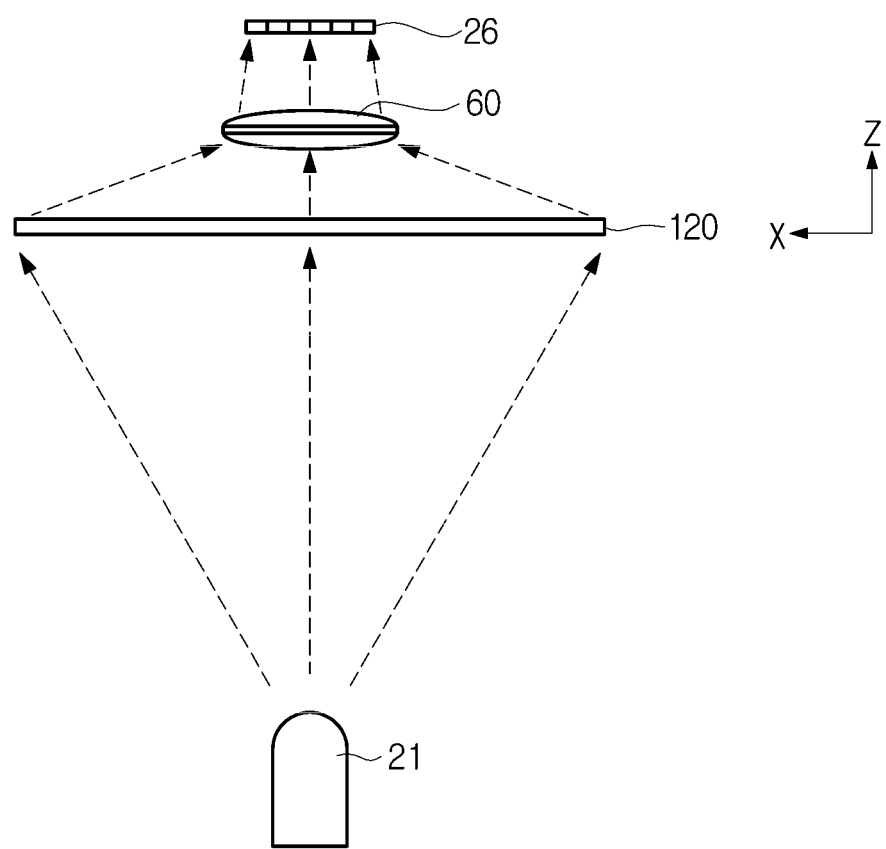
FIG. 17 is a schematic diagram illustrating operations of a test apparatus including a condenser lens according to an exemplary embodiment.

FIG. 17 is a schematic diagram illustrating operations of a test apparatus including a condenser lens according to an exemplary embodiment.

FIG. 17 is a lateral view of the test apparatus 200 in which the light emitter 21 emits light to the inspector 120, and then the light passed through the inspector 120 is passed through the condenser lens 60 to reach the light receiver 26.

The condenser lens 60 may focus light passed through the inspector 120 to reach the light receiver 26. By using the light receiver 26 having a small area, a map related to the inspector 120 having an area larger than that of the light receiver 26 may be acquired. That is, in portion (c) of FIG. 13, the light receiver 24 having an area equal to or larger than that of the inspector 120 may acquire a map by receiving light passed through the inspector 120 without scanning the inspector 120. However, the production cost of the light receiver 24 having a large area may be increased. By using the condenser lens 60 of FIG. 17, the light receiver 26 having a small area may acquire a map which is acquired by the light receiver 24 having a large area.

Figure 18:
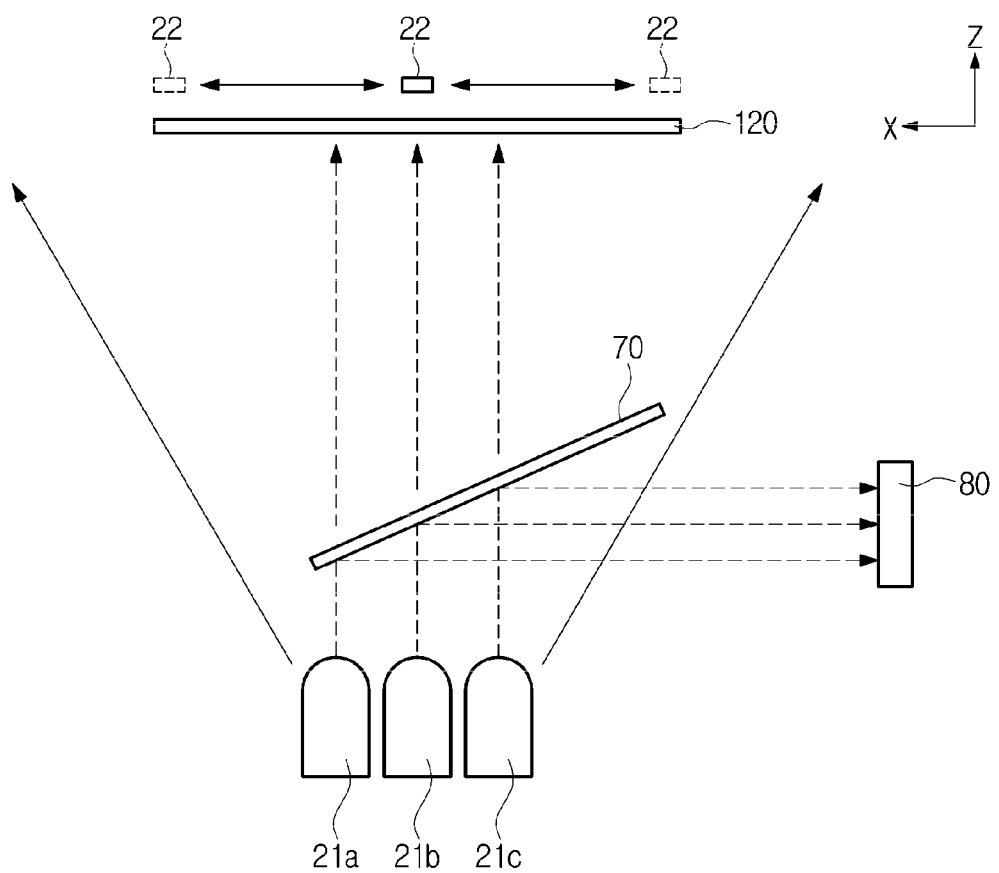
FIG. 18 is a schematic diagram illustrating operations of a test apparatus including a light path changing unit and an auxiliary light receiver, which are configured to compensate for variation of an intensity of light emitted from a light emitter according to an exemplary embodiment.

FIG. 18 is a schematic diagram illustrating operations of a test apparatus including a light path changer and an auxiliary light receiver, which are configured to compensate for variation of an intensity of light emitted from a light emitter according to an exemplary embodiment.

As illustrated in FIG. 18, when light emitted from the light emitter 21 reaches the light receiver 22 scanning the inspector 120 after passing through the inspector 120, a light receiving time difference may occur as the light receiver 22 scans the inspector 120. Accordingly, an intensity of light emitted from the light emitter 21 may be reduced during the time difference. Therefore, the test apparatus 200 may include the auxiliary light receiver 80 configured to receive light emitted from the light emitter 21 to detect the light intensity or variation of amount of light of the light emitter 21. The auxiliary light receiver 80 may be, for example, a photo diode configured to monitor an amount of light.

As illustrated in FIG. 18, the auxiliary light receiver 80 may be disposed adjacent to the light emitter 21, and may include the light path changer 70 configured to change a light path to allow light emitted from the light emitter 21 together with light introduced into the inspector 120 to be received at the auxiliary light receiver 80. That is, light emitted from the light emitter 21 may pass through the light path changer 70 and may be emitted to the inspector 120. In addition, light emitted from the light emitter 21 may be received at the auxiliary light receiver 80 after a path of the light is changed in the light path changer 70. The light path changer 70 may be a changer in a shape of a glass plate having a reflector to penetrate light emitted from the light emitter 21 while changing the path. When the single light emitter 21 is provided, as mentioned above, the reduction of light intensity, in which the light is received according to scanning of the light receiver 22, may be detected as time passes. When the plurality of light emitters 21a, 21b, and 21c is provided, the reduction of light intensity, in which the light is emitted from the plurality of light emitters 21a, 21b, and 21c, may be detected as time passes. The position and shape of the light path changer 70 and the auxiliary light receiver 80 are not limited thereto. Various arrangements may be allowed according to various exemplary embodiments.

The auxiliary light receiver 80 may receive light emitted from the light emitter 21 and may send the light to the processor 30. The processor 30 may compensate for reduced amount of the light intensity by detecting a light intensity transmitted from the auxiliary light receiver 80. That is, the processor 30 may determine how much of the light intensity is reduced by comparing predetermined reference data related to an intensity of light emitted from the light emitter 21 stored in the memory 90 with an intensity of light transmitted from the auxiliary light receiver 80. The predetermined reference data may be data related to how much of a reference light intensity of light emitted from the light emitter 21 and an intensity of light are reduced as time passes. The processor 30 may compensate for a difference based on the variation of the light intensity compared with the reference data, and may apply compensated value when measuring a light intensity passed through a position or an area of the chamber 125 intended to be measured.

Figure 19:
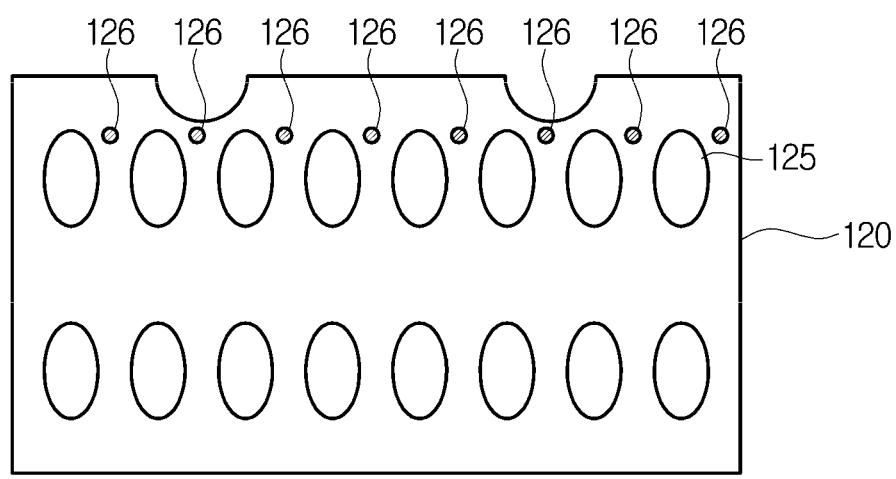
FIG. 19 is a schematic diagram illustrating holes provided in an inspector to compensate for variation of an intensity of light emitted from a light emitter according to an exemplary embodiment.

FIG. 19 is a schematic diagram illustrating holes provided in an inspector to compensate for variation of an intensity of light emitted from a light emitter according to an exemplary embodiment.

As illustrated in FIG. 18, the test apparatus 200 may include the auxiliary light receiver 80 configured to receive light emitted from the light emitter 21 to detect the light intensity or variation of amount of light of the light emitter 21. However, referring to FIG. 19, instead of installing an additional auxiliary light receiver, separated air-holes 126 may be provided adjacent to the chambers 125 of the inspector 120, and the light receiver 22 may receive light passed through the air-holes 126 so that the light intensity or variation of amount of light of the light emitter 21 may be detected. Each of the air-holes 126 configured to detect the variation of the light intensity may be an air hole configured to pass through light without applying reagent unlike the chamber 125. The light passed through the air-holes 126 may be received by the light receiver 22 and then may be transmitted to the processor 30. The processor 30 may compensate for reduced variation of the light intensity of the light emitter 21.

Figure 20:
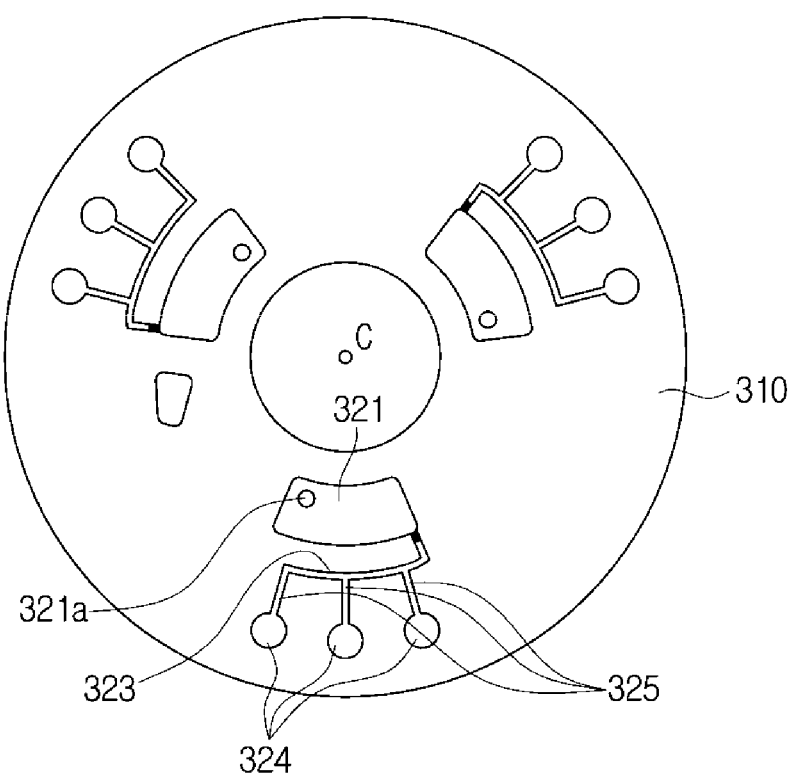
FIG. 20 is a view illustrating an exterior of a reactor according to another exemplary embodiment.

FIG. 20 is a view illustrating an exterior of a reactor according to another exemplary embodiment.

Referring to FIG. 20, the reactor may be a microfluidic device 300 in a shape of a lab-on-a-disk as well as a microfluidic device in a shape of a lab-on-a-chip of FIG. 1. The microfluidic device 300 includes a rotatable platform 310 and microfluidic structures formed in the platform 310.

Each of the microfluidic structures includes a plurality of chambers in which a sample or reagent is accommodated, and a channel that connects the plurality of chambers. The microfluidic structures are formed in the microfluidic device 300. The microfluidic device 300 is formed of a transparent material, and when the microfluidic device 300 is viewed from the above, microfluidic structures formed in the microfluidic device 300 may be seen.

The platform 310 may be formed of a material which is easily formed and of which surface is biologically inactive. For example, the platform 310 may be formed of one of various materials, such as a plastic material, for example, PMMA, PDMS, PC, PP, PVA, and PE, glass, mica, silica, and a silicon wafer.

However, exemplary embodiments are not limited thereto. Any type of material having chemical and biological stability and mechanical processability may be the material of the platform 310, and when a test result within the microfluidic device 300 is optically analyzed, the platform 310 may further have optical transparency.

The microfluidic device 300 may move materials within the microfluidic structures using a centrifugal force caused by rotation. In FIG. 20, the disk-shaped platform 310 is shown. However, the platform 310 may have, for example, a fan shape as well as a full disk shape or a polygonal shape that may be rotatable.

The microfluidic structures may not be structures having a particular shape, but may be structures, such as chambers or channels formed on the platform 310, or may also be comprehensively materials that perform functions as needed. The microfluidic structures may perform different functions according to characteristics of arrangement or types of accommodated materials.

The platform 310 includes a sample inlet 321a, a sample supply chamber 321 in which a sample injected into the sample inlet 321a is accommodated and is supplied to another chamber, a reagent chamber 324 in which the reagent and the sample are reacted, and a distribution channel 323 that distributes the sample accommodated in the sample supply chamber 321 into the reagent chamber 324. Also, when blood is used as the sample, a microfluidic structure for centrifugal separation of blood may be further provided in the microfluidic device 300 as needed.

As illustrated in FIG. 20, when a plurality of reagent chambers 324 is provided, a plurality of branch channels 325 may be diverged from the distribution channel 323, and may connect the distribution channel 323 to each reagent chamber 324.

In the reagent chamber 324, the reagent used to detect target material may be stored in advance. For example, any one of the plurality of the reagent chambers 324 may accommodate a first reagent 1, and a remaining reagent chamber may accommodate a second reagent 2.

The platform 310 may include a plate having a plurality of layers. For example, when the platform 310 includes two plates, i.e., an upper plate and a lower plate, an intaglio structure corresponding to the microfluidic structure, such as a chamber or channel, is formed on a surface on which the upper plate and the lower plate contact each other. The two plates are bonded to each other so that a space in which a fluid may be accommodated and a path on which the fluid may move, may be formed in the platform 310. Bonding of the plates may be performed using one of various methods, such as, for example, adhesion using an adhesive or a double-sided adhesive tape, ultrasonic fusion, and laser welding.

In order to store the reagent in the reagent chamber 324, the first reagent 1 and the second reagent 2 may be accommodated onto a portion in which the intaglio structure corresponding to the reagent chamber 324 of the upper plate or lower plate of the platform 310 is formed, and then the upper plate and the lower plate may be bonded. Also, the accommodated reagent may be dried before the upper plate and the lower plate are bonded to each other.

Figure 21:
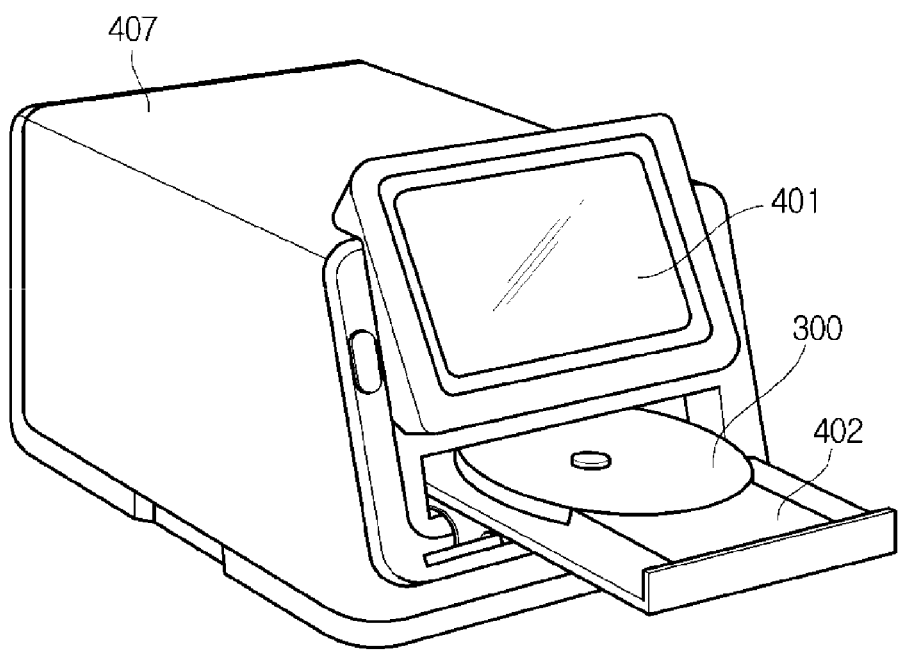
FIG. 21 is a view illustrating an exterior of a test apparatus according to another exemplary embodiment.

FIG. 21 is a view illustrating an exterior of a test apparatus 400 according to another exemplary embodiment. The test apparatus 400 is used to test the microfluidic device 300.

Referring to FIG. 21, the microfluidic device 300 may be placed in a tray 402 of the test apparatus 400. The placed microfluidic device 300 may be inserted into a body 407 of the test apparatus 400 together with the tray 402. When the microfluidic device 400 is inserted into the body 407, the test apparatus 400 rotates the microfluidic device 300 according to a predetermined sequence according to the type of the inserted microfluidic device or the kind of test, and the sample injected into the sample supply chamber 321 is moved to the reagent chamber 324 due to a centrifugal force. The test apparatus 400 further includes an interface 401 that a user may use to control the test.

When the reaction is completed in the reagent chamber 324, an optical property or an electrical property of a result of reaction occurring in the reagent chamber 224 in which reagent is stored may be measured by using a light emitter 452 and a light receiver 453a (refer to FIG. 22) provided inside the test apparatus 400.

Figure 22:
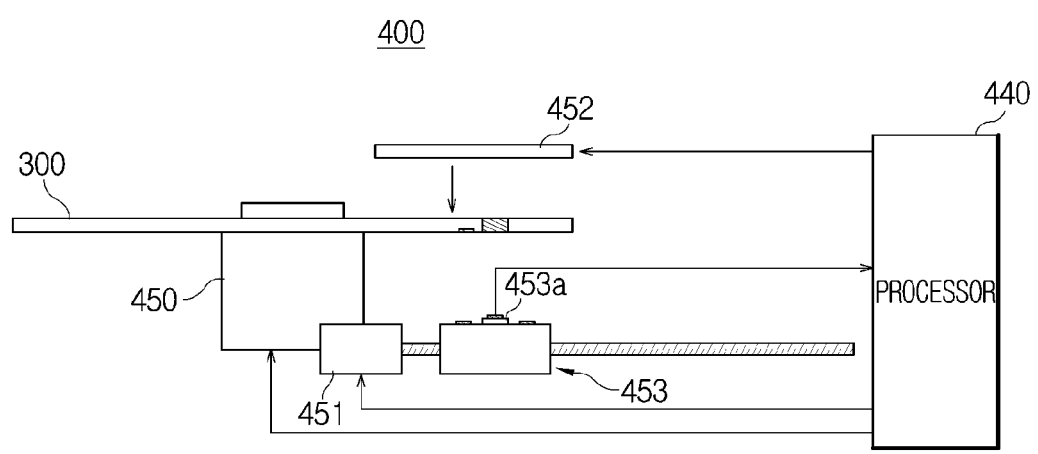
FIG. 22 is a lateral view schematically illustrating a configuration of the test apparatus of FIG. 21.

FIG. 22 is a lateral view illustrating a configuration of the test apparatus 400 of FIG. 21.

Referring to FIG. 22, the test apparatus 400 may include a rotation driving unit 450 rotating the reactor 300, the light emitter 452 emitting light to the reactor 300, a detection module 453 mounted to the light receiver 453a to detect an optical property or an electrical property of a result of reaction occurring in the reagent chamber 224 in which reagent is store by using light emitted from the light emitter 452, a detection module driving unit 451 moving the detection module 453 in a radial direction, and a processor 440 controlling entire operations and functions of the test apparatus 400.

The rotation driving unit 450 may be realized by a spindle motor, and when the reactor 300 is loaded, the rotation driving unit 450 may be driven to drive the reactor 300 under control of the processor 440. The rotation driving unit 450 may receive signals outputted from the processor 440 and may move the reactor 300 to a desired position by repeating rotation and stop motions.

The light emitter 452 may be realized by a planar light source having a great light emission area to uniformly emit light over an area of the reactor 300. For example, the light emitter 452 may be a backlight.

The light emitter 452 and the light receiver 453a may be provided in the same direction, or may be formed to be opposite type to face each other, as illustrated in FIG. 22. In FIG. 22, the light emitter 452 and the light receiver 453a are provided on an upper portion of the reactor 300 and a lower portion of the reactor 300, respectively with respect to the reactor 300, but position thereof may be switched off. The light emitter 452 may adjust an amount of emission light under the control of the processor 440.

The light receiver 453a may receive light emitted from the light emitter 452 and passed through the reactor 300, and the light receiver 453a may be realized by CMOS image sensor or CCD image sensor.

In the test apparatus 400, the light receiver 453a may be installed in the detection module 453, which is a device unit to be movable in a radial direction, to receive light emitted from the light and passed through the reactor 300 by using the single light receiver 453a.

When the light receiver 453a acquires light passed through the reactor 300, the processor 440 may calculate detection results of test items, which are different to each other, based on each detection results detected by the light receiver 453a. Because the purpose and the effect of the test apparatus 400 including the reactor 300 in a shape of a lab-on-a-disk may be similar with that of the test apparatus 200 including the reactor 100 in a shape of a lab-on-a-chip, description thereof will be omitted.

Figure 23:
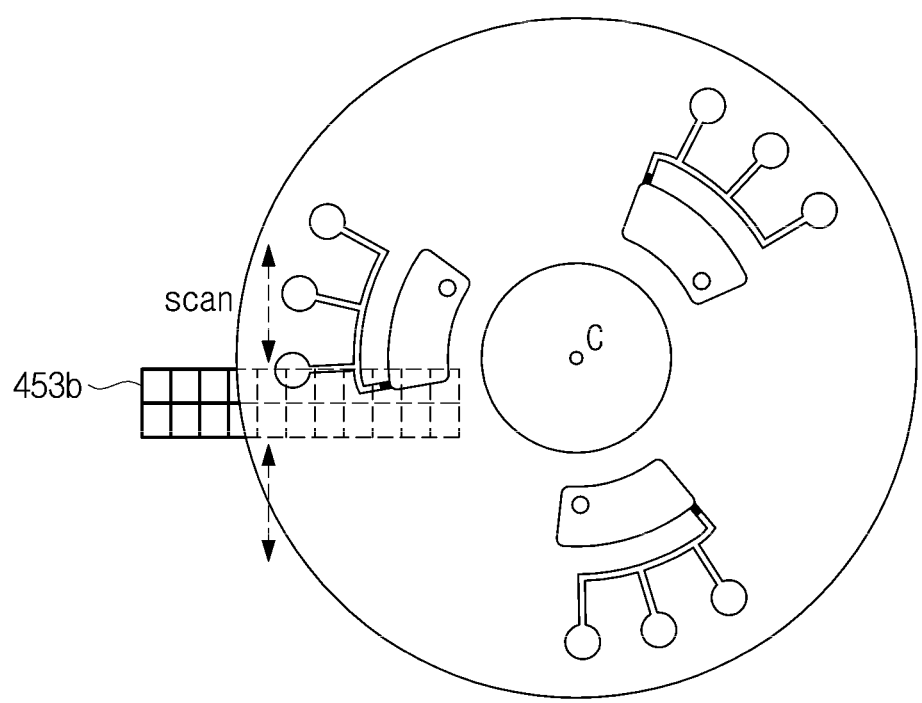
FIG. 23 is a schematic diagram illustrating operations of a test apparatus according to another exemplary embodiment.

FIG. 23 is a schematic diagram illustrating operations of a test apparatus according to another exemplary embodiment.

As illustrated in FIG. 23, light emitted from the light emitter 452 and passed through the chamber 324 of the reactor 300 may be received by the light receiver 453b, and information related to the received light may be transmitted to the processor 440. The processor 440 may measure an optical density based on the received information. As illustrated in FIG. 23, operations of the test apparatus may be applied to the test apparatus 400 including the reactor 300 in a shape of a lab-on-a-disk, and detailed operation process may be the same as that of the test apparatus 200 including the reactor 100 in a shape of a lab-on-a-chip, as illustrated in FIGS. 1 to 19. Accordingly, a duplicate description thereof will be omitted. However, in FIG. 23, the reactor 300 may have a disk shape, and thus operations illustrated in the exemplary embodiments may be realized by rotation of the reactor 300 or by scanning the reactor 300 by the light receiver 453b.

According to the exemplary embodiment described above, it may be possible to reduce differences between blood analysis devices (point-of-care) based on a lab-on-a-chip or a lab-on-a-disk. In addition, it may be possible to improve the accuracy and reproducibility by measuring an optical density precisely and accurately regardless of an arrangement state of a test cartridge. That is, a test apparatus may accurately detect a position of a detection chamber to measure an optical density in the same position within each detection chamber even when an optical detection apparatus and an arrangement state of a cartridge are changed in every test.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary embodiments and are not to be construed as limiting the exemplary embodiments. The exemplary embodiments can be readily applied to other types of devices. Also, the description of the exemplary embodiments is intended to be illustrative, and not to limit the scope of the claims, and many alternatives, modifications, and variations will be apparent to those skilled in the art.

What is claimed is:

1. A test apparatus configured to test a sample in a reactor, the test apparatus comprising:
   at least one light emitter configured to emit light to chambers included in the reactor, each of the chambers being configured to include a portion of the sample;
   a light receiver configured to receive light passed through the chambers, while moving in a direction from a side of the reactor to another side of the reactor;
   a motor configured to move the light receiver in the direction from the side of the reactor to the other side of the reactor; and
   a processor configured to:
      generate a map comprising coordinates respectively of the chambers, based on light receiving positions at which the light receiver receives the light passed through the chambers, the light receiving positions being along the direction from the side of the reactor to the other side of the reactor, and further based on intensities of the light received respectively at the light receiving positions, the coordinates comprising respectively pixel numbers of light receiving elements and the light receiving positions;
      determine a position or an area of a chamber among the chambers, based on the light receiving positions and the intensities; and measure an optical density of light passed through the determined position or the determined area of the chamber.

2. The test apparatus according to claim 1, wherein the light receiver comprises an array of the light receiving elements.

3. The test apparatus according to claim 2, wherein the array comprises a one-dimensional array or a two-dimensional array.

4. The test apparatus according to claim 1, wherein the processor is further configured to calculate an average value of an optical density of light passed through an area within a range from the determined position or the determined area of the chamber.

5. The test apparatus according to claim 1, wherein the light emitter is further configured to emit the light to the chambers at a fixed position, or while moving in the direction from the side of the reactor to the other side of the reactor in correspondence to the light receiver.

6. The test apparatus according to claim 1, further comprising:
    a filter configured to:
        detect light having wavelengths from the emitted light; and
        emit the detected light to the chambers.

7. The test apparatus according to claim 1, further comprising:
    an auxiliary light receiver configured to receive the emitted light.

8. The test apparatus according to claim 7, further comprising:
    a light path changer configured to change a path of the emitted light to allow the auxiliary light receiver to receive the emitted light.

9. The test apparatus according to claim 7, wherein the processor is further configured to compensate for differences of a variation of an intensity of the light received through the chambers by comparing a variation of an intensity of the received emitted light with data of an intensity of the emitted light.

10. The test apparatus according to claim 9, wherein the processor is further configured to measure the optical density of the light passed through the determined position and the determined area of the chamber, based on the compensated differences.

11. The test apparatus according to claim 1, further comprising:
    a condenser lens disposed between the reactor and the light receiver, the condenser lens being configured to focus the light passed through the chambers to the light receiver having an area less than that of the reactor.

12. A test apparatus configured to test a sample in a reactor, the test apparatus comprising:
    at least one light emitter configured to emit light to chambers included in the reactor, each of the chambers being configured to include a portion of the sample;
    a light receiver comprising light receiving elements configured to receive light passed through the chambers, while moving in a direction from a side of the reactor to another side of the reactor;
    a motor configured to move the light receiver in the direction from the side of the reactor to the other side of the reactor; and
    a processor configured to:
        generate a map comprising coordinates respectively of the chambers, based on light receiving positions at which the light receiver receives the light passed through the chambers, the light receiving positions being along the direction from the side of the reactor to the other side of the reactor, and further based on intensities of the light received respectively at the light receiving positions, the coordinates comprising respectively pixel numbers of the light receiving elements and the receiving positions;
        determine a coordinate of a chamber among the chambers, the coordinate comprising a pixel number of one of the light receiving elements and a light receiving position of the light receiver, at which the one of the light receiving elements receives a largest intensity of the light passed through the chambers, the light receiving position being along the direction from the side of the reactor to the other side of the reactor.

13. The test apparatus of claim 12, wherein the processor is further configured to measure an optical density of light passed through the determined coordinate of the chamber.

14. The test apparatus of claim 12, wherein the light receiver is further configured to receive light passed through air-holes adjacent to the chambers, and
    the processor is further configured to compensate for differences of a variation of an intensity of the light received through the chambers by comparing a variation of an intensity of the light received through the air-holes with data of an intensity of the emitted light.

* * * * *